US010835694B2

(12) United States Patent
Lastow et al.

(10) Patent No.: US 10,835,694 B2
(45) Date of Patent: Nov. 17, 2020

(54) DRY POWDER INHALER

(71) Applicant: Iconovo AB, Lund (SE)

(72) Inventors: Orest Lastow, Torna Haellestad (SE); Peter Jennfors, Limhamn (SE)

(73) Assignee: Iconovo AB, Lund (SE)

( * ) Notice: Subject to any disclaimer, the term of this patent is extended or adjusted under 35 U.S.C. 154(b) by 300 days.

(21) Appl. No.: 15/572,493

(22) PCT Filed: May 9, 2016

(86) PCT No.: PCT/EP2016/060272
§ 371 (c)(1),
(2) Date: Nov. 7, 2017

(87) PCT Pub. No.: WO2016/180752
PCT Pub. Date: Nov. 17, 2016

(65) Prior Publication Data
US 2018/0110942 A1    Apr. 26, 2018

(30) Foreign Application Priority Data

May 8, 2015 (SE) ..................................... 1550591
May 8, 2015 (SE) ..................................... 1550592
May 8, 2015 (SE) ..................................... 1550593

(51) Int. Cl.
*A61M 15/00*    (2006.01)

(52) U.S. Cl.
CPC .... *A61M 15/0095* (2014.02); *A61M 15/0003* (2014.02); *A61M 15/0065* (2013.01);
(Continued)

(58) Field of Classification Search
CPC ........... A61M 15/0003–0008; A61M 15/0081; A61M 2205/276; A61M 15/0048;
(Continued)

(56) References Cited

U.S. PATENT DOCUMENTS 6,116,238 A * 9/2000 Jackson ............ A61M 15/0045
128/203.12
6,439,227 B1 * 8/2002 Myrman ........... A61M 15/0091
128/200.14
(Continued)

FOREIGN PATENT DOCUMENTS

CN         1684731 A    10/2005
CN       102711885 A    10/2012
(Continued)

OTHER PUBLICATIONS

Chinese Search Report dated Feb. 23, 2020 for copending Chinese Application No. 201680026757.5.
(Continued)

*Primary Examiner* — Annette Dixon
(74) *Attorney, Agent, or Firm* — Fishman Stewart PLLC

(57) ABSTRACT

A dry powder medicament inhaler for metering an inhalation of dry powdered medicament may include at least one inlet and at least one outlet, wherein a communication between said inlet and outlet at least includes a mixing and deaggregation chamber and at least two dosage communications between the inlet and the chamber. The inhaler may also include a dosage mechanism for arranging at least one dose of a medicament between the inlet and the chamber, such that said at least one dose may be delivered upon inhalation at said outlet through said communications. The inhaler may further include a locking mechanism, wherein on moving the dosage mechanism from a dose collecting position to a dose administering position the locking mechanism may be moved from an unlocked to a locked position preventing the metering of any further doses prior to resetting of the locking mechanism. Instead of a locking mechanism, the inhaler may include a dosage indicator or a counterweight mechanism. The inhaler may also include combinations of a
(Continued)

locking mechanism, a dosage indicator, and a counterweight mechanism.

25 Claims, 24 Drawing Sheets

(52) U.S. Cl.
CPC ..... *A61M 15/0075* (2014.02); *A61M 15/0005* (2014.02); *A61M 15/0008* (2014.02); *A61M 2205/21* (2013.01); *A61M 2205/276* (2013.01); *A61M 2205/32* (2013.01); *A61M 2205/582* (2013.01); *A61M 2205/583* (2013.01); *A61M 2205/584* (2013.01); *A61M 2205/587* (2013.01)

(58) Field of Classification Search
CPC .......... A61M 15/0005; A61M 15/0006; A61M 15/0008; A61M 15/0015; A61M 15/0025; A61M 15/0026; A61M 15/0031; A61M 15/0033; A61M 15/0043; A61M 15/0045; A61M 15/0065; A61M 15/0066; A61M 15/0071; A61M 15/0073; A61M 15/0075; A61M 15/008; A61M 15/0083; A61M 15/0086; A61M 15/0091; A61M 15/0095; A61M 15/02; A61M 2016/0024; A61M 2202/0007; A61M 2202/062; A61M 2202/064; A61M 2205/18; A61M 2205/21; A61M 2205/32; A61M 2205/52; A61M 2205/582; A61M 2205/583; A61M 2205/584; A61M 2205/587; A61M 2205/6045; A61M 2206/16; G06M 1/04; G06M 1/045; G06M 1/248

USPC .......................................................... 604/58
See application file for complete search history.

(56) References Cited

U.S. PATENT DOCUMENTS

| | | |
|---|---|---|
| 2002/0100478 A1 | 8/2002 | Prime et al. |
| 2002/0170560 A1* | 11/2002 | Young ............... A61M 15/0045 128/203.15 |
| 2002/0189615 A1* | 12/2002 | Henry ............... A61M 15/0045 128/203.21 |
| 2004/0025874 A1* | 2/2004 | Seppl ................ A61M 15/0065 128/203.15 |
| 2005/0183723 A1* | 8/2005 | Pinon ................ A61M 15/0075 128/203.15 |
| 2006/0185672 A1 | 8/2006 | Pinon et al. |
| 2012/0304991 A1* | 12/2012 | Gotliboym ........ A61M 15/0003 128/203.15 |

FOREIGN PATENT DOCUMENTS

| | | |
|---|---|---|
| WO | WO-01/76668 | 10/2001 |
| WO | 2004026380 A2 | 4/2004 |
| WO | 2009046215 A2 | 4/2009 |
| WO | 2009046215 A3 | 7/2009 |
| WO | WO-2011/059953 | 5/2011 |

OTHER PUBLICATIONS

Chinese Office Action dated Mar. 3, 2020 for copending Chinese Application No. 201680026757.5.

* cited by examiner

DRY POWDER INHALER

CROSS-REFERENCE TO RELATED APPLICATIONS

This application claims priority to International Patent Application No. PCT/EP2016/060272, filed on May 9, 2016, Swedish Patent Application No. 1550592-8, filed on May 8, 2015, Swedish Patent Application No. 1550591-0, filed on May 8, 2015, and Swedish Patent Application No. 1550593-6, filed on May 8, 2015, the contents of all of which are incorporated herein by reference in their entireties.

TECHNICAL FIELD

This invention pertains in general to the field of medicament inhalers, and more particularly to dry powder inhalers. The inhaler may comprise a locking mechanism such that inhalation of any previously metered medicament is required prior to a further dose being administrable. Alternatively, the inhaler comprises an indicator for determining if any previously metered medicament is yet to be inhaled. The inhaler may alternatively comprise a counterweight mechanism for maintaining an incorrect dose prevention mechanism in a position.

BACKGROUND

In the pharmaceutical field, with respect to treatment of respiratory and/or other diseases, inhalers have been widely used. Numerous drugs, medications and other substances are inhaled into the lungs for rapid absorption in the blood stream and for local action in the lung with such inhalers.

Inhaled drugs fall into two main categories, in form of liquids, including suspensions, and powders. The choice of category depends on the characteristics of the drugs, medications, etc., to be inhaled.

The most common type of inhaler is the pressurized metered-dose inhaler. In this type of inhaler medication is most commonly stored in solution in a pressurized canister that contains a propellant, although it may also be a suspension. The canister is attached to a plastic, hand-operated actuator. On activation, the metered-dose inhaler releases a fixed dose of medication in aerosol form.

Another kind of inhaler is a nebulizer, which supply medication as an aerosol created from an aqueous formulation.

The kind referred to herein is yet another type, in form of a dry powder inhaler. A dry powder inhaler releases a pre-metered, capsuled, dose or a device-metered dose of powdered medication that is inhaled through the inhaler. Inhalers with device-metered dose of powdered medication are normally inhalers with medication reservoir, containing powdered medication, from which metered doses are withdrawn through the use of different dose metering arrangements, said doses then being inhaled.

In many dry powder inhalers the actuation of the metering is controlled by the user and there is a risk that the user can meter multiple doses in to a dose administering location without first inhaling these doses. This misuse can be either deliberate or inadvertent, however, in some cases it can lead to the user receiving a greater dose than necessary through the inhaler. In others it can lead to the user not receiving a dose at all if the user has not managed to meter a dose correctly. Any system for ensuring that a user receives the correct number of doses must be reliable in that it should not be possible to reset unintentionally.

SUMMARY

Accordingly, the present invention preferably seeks to mitigate, alleviate or eliminate one or more of the above-identified deficiencies in the art and disadvantages singly or in any combination and solves at least the above mentioned problems by providing in a first aspect a dry powder medicament inhaler for metering an inhalation of dry powdered medicament comprising: at least one inlet and at least one outlet, wherein a communication between said at least one inlet and said at least one outlet at least comprises a mixing and deaggregation chamber and at least two dosage communications between the at least one inlet and the chamber; a dosage mechanism for arranging at least one dose of a medicament between the inlet and the chamber, such that said at least one dose may be delivered upon inhalation at said outlet through said communications; a locking mechanism wherein on moving the dosage mechanism from a dose collecting position to a dose administering position the locking mechanism is moved from an unlocked to a locked position preventing the metering of any further doses prior to resetting of the locking mechanism.

In a second aspect there is provided a dry powder medicament inhaler for metering an inhalation of dry powdered medicament comprising: at least one inlet and at least one outlet, wherein a communication between said at least one inlet and said at least one outlet at least comprises a mixing and deaggregation chamber and at least two dosage communications between the at least one inlet and the chamber; a dosage mechanism for arranging at least one dose of a medicament between the inlet and the chamber, such that said at least one dose may be delivered upon inhalation at said outlet through said communications; a dosage indicator wherein on moving the dosage mechanism from a dose collecting position to a dose administering position the dosage indicator is displayed indicating that a dose is ready to be inhaled.

In a third aspect there is provided a dry powder medicament inhaler for metering an inhalation of dry powdered medicament comprising: at least one inlet and at least one outlet, wherein a communication between said at least one inlet and said at least one outlet at least comprises a mixing and deaggregation chamber and at least two dosage communications between the at least one inlet and the chamber; a dosage mechanism for arranging at least one dose of a medicament between the inlet and the chamber, such that said at least one dose may be delivered upon inhalation at said outlet through said communications; a incorrect dose prevention mechanism wherein on moving the dosage mechanism from a dose collecting position to a dose administering position the incorrect dose prevention mechanism is activated and moved to an outer, preventing position; and, a pivotable counterweight associated with the incorrect dose prevention mechanism such that the pivotable counterweight inhibits the activation of the incorrect dose prevention mechanism.

Advantageous embodiments of the inhaler are described below and in the appended dependent claims.

BRIEF DESCRIPTION OF THE DRAWINGS

These and other aspects, features and advantages of which the invention is capable of will be apparent and elucidated from the following description of embodiments of the present invention, reference being made to the accompanying drawings, in which.

DETAILED DESCRIPTION

A skilled person will understand that the dry powder inhalers of the embodiments described below with reference to the figures are all generally similar in their overall design and differ only in the presence of a locking mechanism, a dosage indicator, or an incorrect dose prevention mechanism. However, as will become clearer below the dry powder inhaler may have two or all three of a locking mechanism, a dosage indicator, or an incorrect dose prevention mechanism. For instance, in the description of FIGS. 18 and 19, the incorrect dose prevention mechanism of the dry powder medicament inhaler may also be a locking mechanism. Moreover, as will be described in respect of FIGS. 17 to 24, the incorrect dose prevention mechanism of the dry powder inhaler can also be both a combined indicating and a locking mechanism. It is also disclosed that in the dry powder inhaler comprising a dosage indicator of FIGS. 9 to 16, the dosage indicator can simultaneously be a locking mechanism as described in the dry powder inhaler of FIGS. 1 to 8.

Dry Powder Inhaler Comprising a Locking Mechanism—FIGS. 1 to 8

The following description of one embodiment of the present invention describes a dry powder inhaler comprising a locking mechanism in association with a dose disk preventing the metering of medicament via the dose disk prior to inhalation of any previously metered medicament.

Figure 1A:
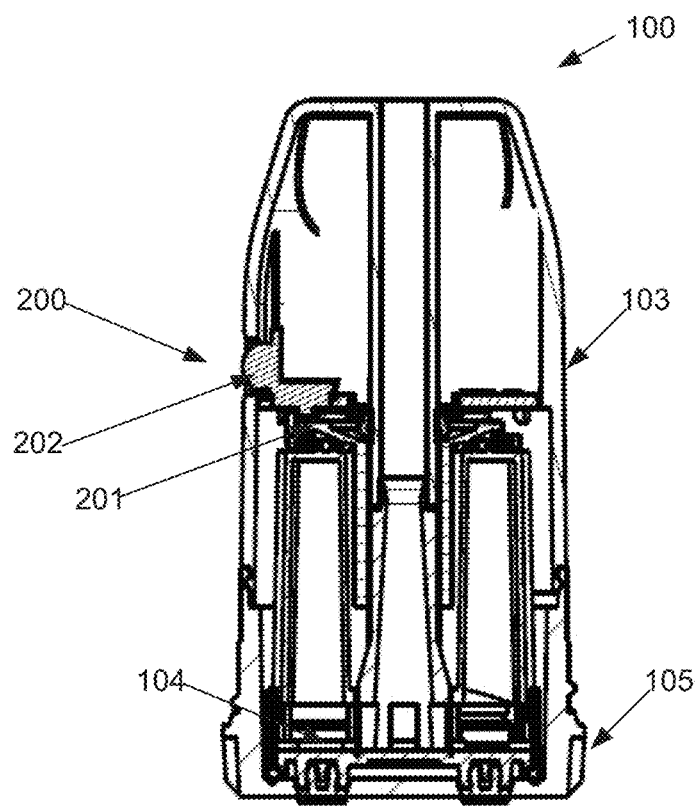
FIG. 1a is a perspective and cross-sectional view of the dry powder inhaler according to an embodiment of the first aspect of the invention.
Figure 1B:
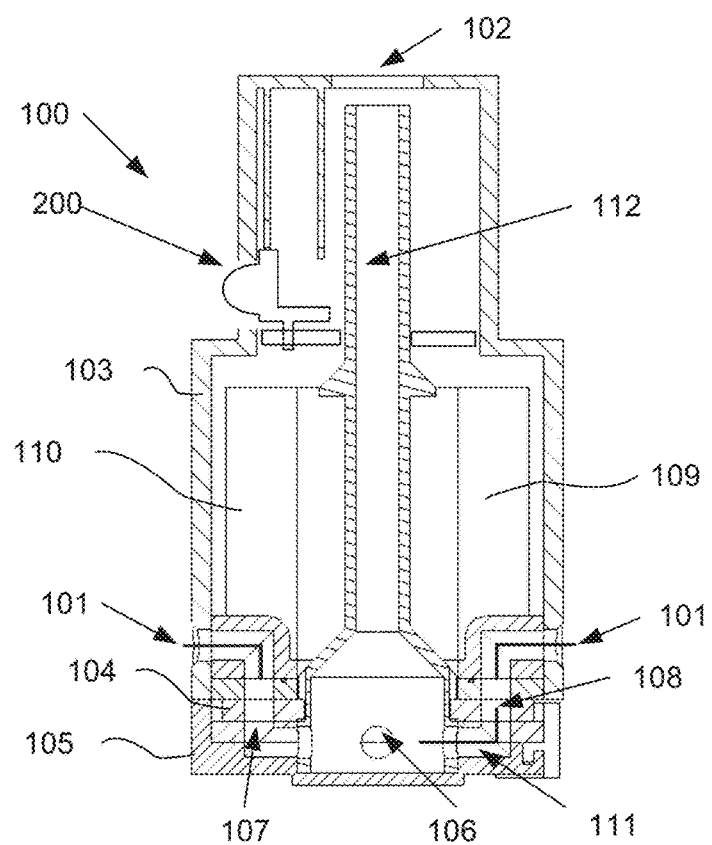
FIG. 1b is a perspective and cross-sectional view of the dry powder inhaler more clearly showing the inlets, outlet, and reservoirs.

FIG. 1 illustrates a dry powder medicament inhaler 100 comprising a locking mechanism 200 for restricting dose metering to a single dose. The dry powder medicament inhaler 100 comprises air inlets 101 and an air outlet 102. The outlet 102 is arranged at a first end of the dry powder drug inhaler 100, while the inlets 101 are arranged at a zone in an opposite second end of the dry powder drug inhaler 100. The outlet 102 is arranged centrally, along the longitudinal axis of the dry powder medicament inhaler 100. The inlets 101 may be arranged at a radial, in relation to the longitudinal axis of the dry powder drug inhaler 100, periphery of the dry powder inhaler 100, such that the inlets 101 lead inhaled air transversally and radially towards the central portion of the dry powder inhaler 100.

The dry powder medicament inhaler 100 comprises an upper proximal reservoir housing 103, a dose disc 104, and a lower distal twister 105. The reservoir housing 103 and the twister 105 cooperate so as to house the dose disc 104 in between these two. The twister 105 cooperates with the dose disc 104, such that the dose disc 104 may be rotated, via rotation and twisting of the twister 105, between a dose administering position and a dose collecting position. This may be accomplished by interconnecting the dose disc 104 and the twister 105 via interconnecting grooves and ribs, or letting the twister 105 extend longitudinally centrally of the dose disc 104 and connected thereto, such as disclosed for example in FIG. 1. Preferably, the rotation of the dose disc 104 has two end positions, corresponding to the dose administering position and the dose collecting position, in its relation with the reservoir housing 103, in a known manner.

In the dose administering position, the inlets 101 are in fluid communication with a mixing and deaggregation chamber 106 via dosage communications 107. The dosage communications 107 then run through openings 108 in the dose disc 104. Hence, the openings 108, in the dose administering position, is superimposed the communications 107. When rotating the dose disc 104 into a dose collecting position, the openings 108 are rotated away from fluid communication with the inlets 101 and the chamber 106. Instead, the openings 108 are rotated into medicament reservoirs 109, 110, wherein the openings 108 may collect a medicament housed in the reservoirs 109, 110. The medicament contained in the medicament reservoir 109 may be a medicament different from the medicament contained in the medicament reservoir 110. Due to the two reservoirs 109, 110, the inhaler 100 may deliver two substances in one inhalation, said two substances otherwise being incompatible, meaning that these two substances not would be possible to be comprised in one joint reservoir, such that a dry powder inhaler device 100 in which effective and satisfactory dispersion of the dry powder is obtained, which inhaler 100 can administer medicament comprising substances which can be incompatible in mixture or for other reasons are preferred to have in separate reservoirs 109,110.

It is possible to arrange the dose disc 104 and the openings 108 thereof such that when a first set of two openings 108 are superimposed the communications 107, i.e. in a dose administering position, a second set of two openings 108 are positioned in the medicament reservoirs 109, 110, respectively. Additionally, the distribution of the openings 108 on the dose disc 104 is such that the dose disc may be rotated in one direction only, which means that when the second set of two openings 108 are superimposed the communications 107, the first set of openings 108 are positioned in the medicament reservoirs 109, 110, respectively.

The dose disc 104 and the openings in the dose disc 108 in combination are hereafter referred to as the dosage mechanism 104, 108.

As the dosage mechanism 104, 108 of the dry powder medicament inhaler 100 is moved from a dose collecting position to a dose administering position the locking mechanism 200 is moved from an unlocked to a locked position preventing the metering of any further doses prior to resetting of the locking mechanism.

The locking mechanism 200 is arranged in association with the dosage mechanism 104, 108 such that the locking mechanism 200 can restrict the dosage mechanism 104, 108 from rotating after a single dose has been metered and thus metering multiple doses. As the twister 105 and the dosage mechanism 104, 108 are interconnected the locking mechanism 200 also restricts the rotational movement of the twister 105.

The locking mechanism 200 can restrict the inadvertent metering of multiple doses in to dose metering reservoirs 109,110 as the locking mechanism must be unlocked prior to metering a new dose into the dose metering reservoirs 109,110. The locking mechanism can also restrict the intentional misuse of the inhaler by requiring the inhalation of a previously metered dose prior to metering any new dose.

Figure 2A:
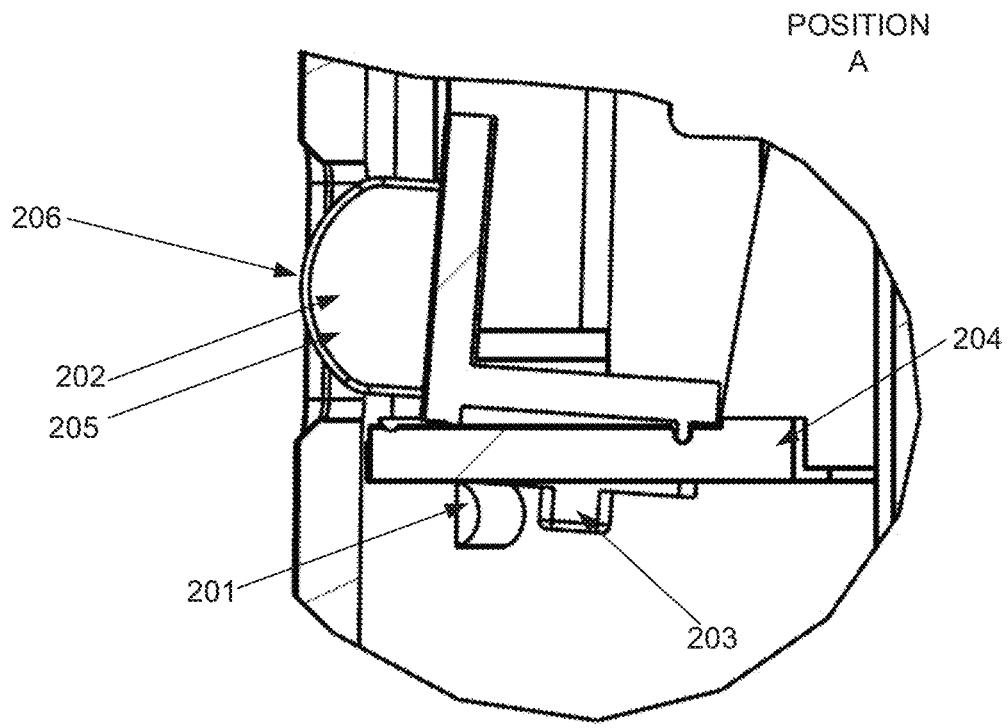
FIG. 2a is a perspective and cut-away view of the locking mechanism in a unlocked position.
Figure 2B:
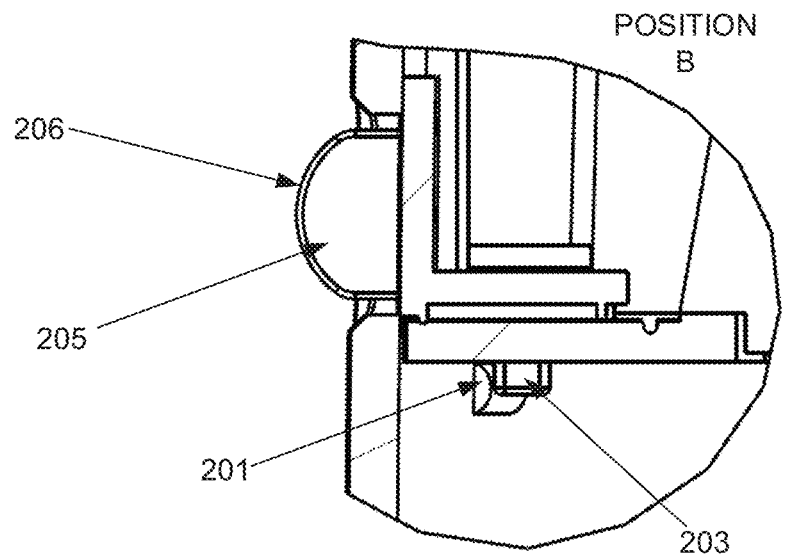
FIG. 2b is a perspective and cut-away view of the locking mechanism in a locked position.

As shown in FIG. 2 the locking mechanism 200 comprises a locking disc 201 and a latch 202. The locking disc 201 is a disc having an axis of rotation aligned with the longitudinal axis of the dry powder medicament inhaler 100. The latch 202 is provided with two end positions. An outer locked position A and an inner unlocked position B.

The latch 202 is associated with the locking disc 201 such that a projection 203 from the latch 202 can, in a locked position A, extend through a plane of the locking disc 201 and be aligned such that it is possible that the projection 203 abuts a member or members of the locking disc 201. One way of achieving this is that the latch 202 can be moved radially inwards towards a central longitudinal axis of the dry powder medicament inhaler to move to an unlocked position and then can be moved radially outwards to move to a locked position. As opposed to the rotation of the locking disc 201 the latch 202 moves along in a substantially linear path. The linear path being a radial line extending from the central longitudinal axis of the dry powder inhaler outwardly perpendicular to the longitudinal axis. The latch 202 can be arranged above the locking disc 201. A substantially flat supporting disc 204 can be located between the latch 202 and the locking disc 201. The supporting disc 204 acts as a guide and a support for the latch 202.

In an unlocked position B, the projection 203 from the latch 202 can also extend through the plane of the locking disc 201 but in an unlocked position the latch 202 does not abut the member or members of the locking disc 201 such that the locking disc 201 can be rotated. One way of achieving this is that the projection 203 of the latch 202 in a locked position A is aligned with circumferential members of the locking disc 201 whereas in an unlocked position B the projection 203 of the latch 202 is out of alignment with the circumferential members of the locking disc such that the locking disc 201 can be rotated. For example, the circumferential members could be the vertical stops 215 disclosed in FIG. 3B.

The locking disc 201 is associated with the dose disc 104 and twister 105 such that rotation of the dose disc 104 or twister 105 causes rotation of the locking disc 201.

The dose disc 104 and the locking disc 201 are arranged substantially parallel and have aligned central axes. The dose disc 104 and the locking disc 201 can be fixed upon a central shaft. The shaft may be sleeve formed and be arranged on the outside of an inhalation chimney 112. Fixing the locking disc 201 and the dose disc 104 to a central shaft means that the dose disc 104 and the locking disc 201 are locked in their rotation. The dose disc 104 and the locking disc 201 may also be associated by other means such that rotation in one disc causes a rotation in the other.

When the latch 202 is in position A the locking disc 201 cannot rotate and thus the dose disc 104 cannot rotate. When the latch is in position B the locking disc 201 and the dose disc 104 can both rotate.

Figure 3A:
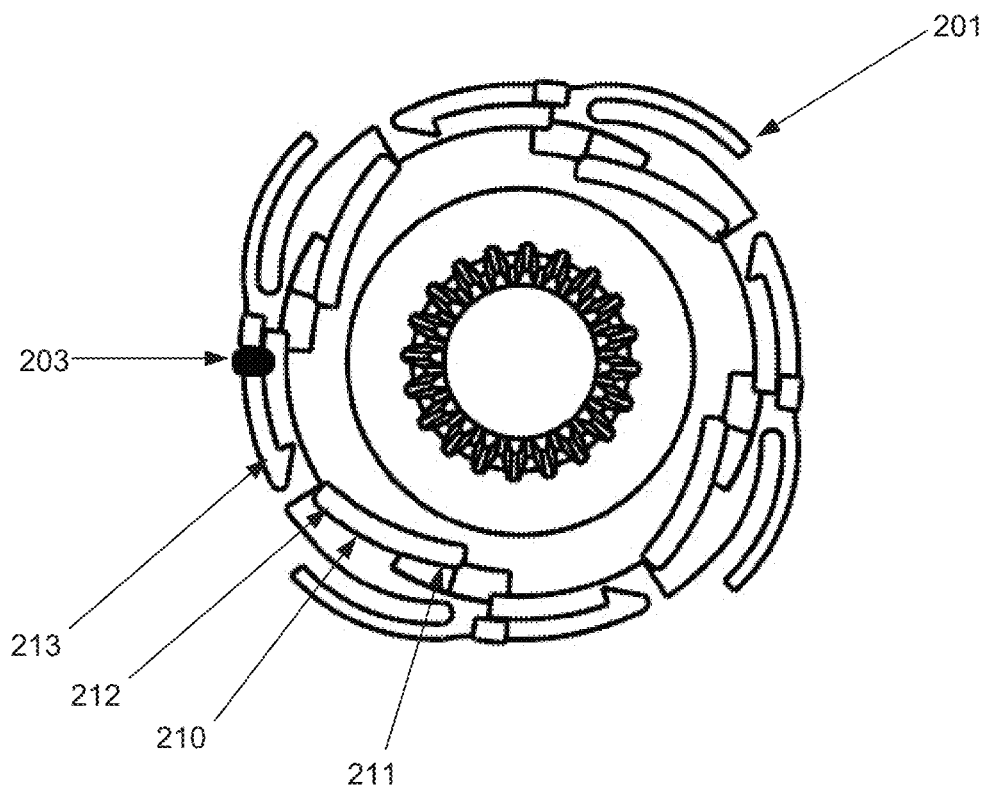
FIG. 3a is a top-down exploded view of the locking disc of the locking mechanism.
Figure 3B:
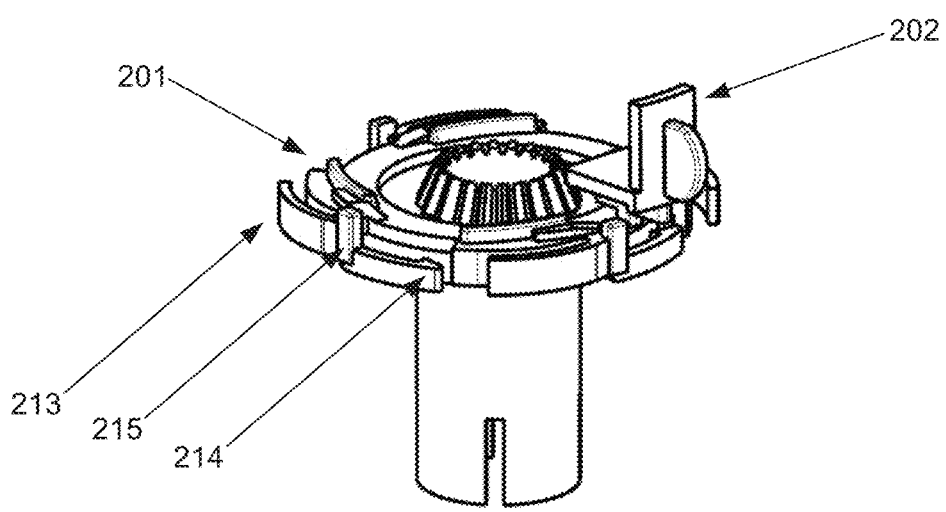
FIG. 3b is a perspective exploded view of the locking disc and latch of the locking mechanism.

The locking disc 201 is shown in FIG. 3. The locking disc comprises guiding members 210 extending at an angle from the circumference of the locking disc 201. The guiding members extend in a plane parallel and aligned with the plane formed by the locking disc 201. The guiding members 210 are arranged such that they are closer to the centre of the locking disc 201 at a first end 211 than at a second end 212. The locking disc 201 further comprises peripheral locking members 213. The peripheral locking members 213 extend from the circumference of the locking disc 201. The peripheral locking members 213 have a base 214 extending parallel to the plane of the locking disc 201 and a vertical stops 215 extending perpendicular to the plane of the locking disc 201. The vertical stop extends 215 substantially vertically. The peripheral locking members 213 are positioned at a distance further from the centre of the locking disc 201 than the guiding members 210. The peripheral locking members are dimensioned such that the projection 203 of the latch 202 can act as a limit to stop any rotation 203 of the locking disc 201 and as they can be fixed to the same shaft, the dose disc 104.

Figure 4A:
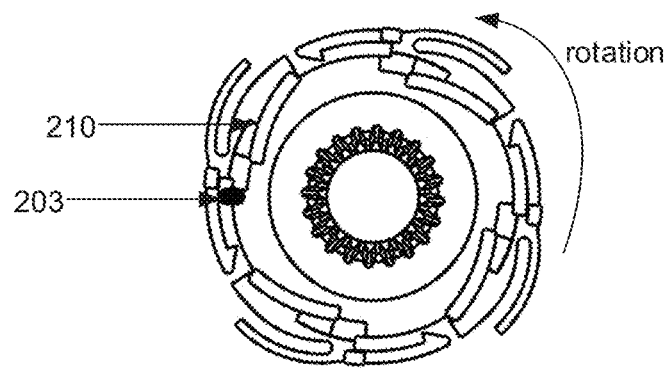
FIGS. 4a-4e are cross sectional exploded views of the locking mechanism focusing on the latch and locking disc during different points of rotation of the locking disc.
Figure 4B:
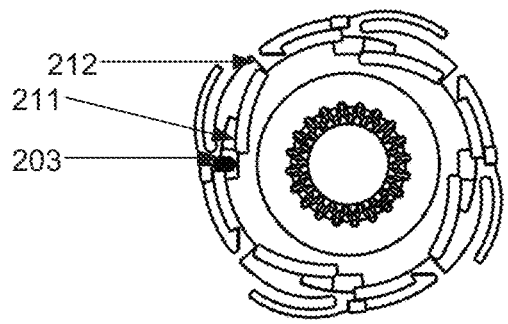
Figure 4C:
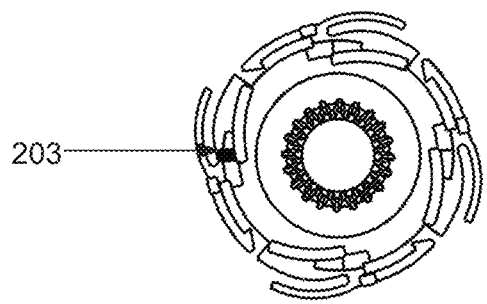
Figure 4D:
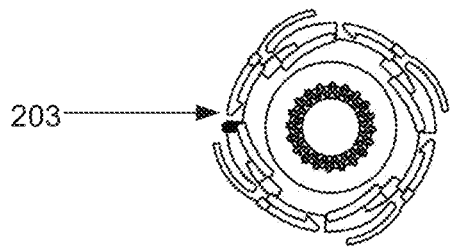

The latch 202 can be moved to a locked position, when the latch 202 is moved from position B to position A. The latch being in position B is shown in a top down view in FIG. 4a, wherein the projection 203 from latch 202 does not interfere with members of the locking disc 201. As the dose disc 104 is rotated the locking disc 201 is also rotated. The first end 211 of the guiding members, being closer to the centre of the locking disc 201, contacts the projection 203 as shown in FIG. 4b. As the dose disc is further rotated the locking disc 201 rotates further and the projection 203 slides along the length of the guiding member 210 towards the second end 212 as shown in FIG. 4c. As the second end 212 of the guiding member 210 is further from the centre of the locking disc, during rotation of the dose disc 104 and the locking disc 201 the projection 203 and the latch 202 are moved outwardly from the centre of the locking disc 201 as shown in FIG. 4d.

During rotation of the dose disc 104 the dose disc moves from a dose collecting position to a dose administering position.

Figure 4E:
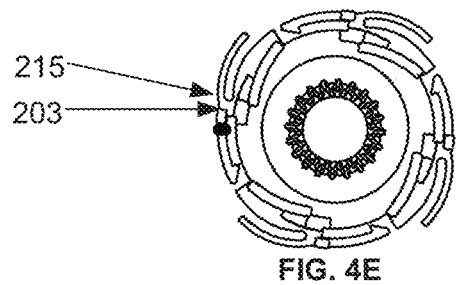

After rotation the latch 202 comprising the projection 203 abuts the vertical stop 215 of the peripheral locking member 213 as shown in FIG. 4e. As the latch 202 is now interfering with members of the locking disc 201 the dose disc 104 and the locking disc 201 cannot be rotated further. The dose disc 104 is thus locked in position.

To enable the dose disc 104 to be rotated again the 202 latch must be moved to position B. The movement of the locking mechanism from a locked position A to an unlocked position B is called resetting the locking mechanism.

Resetting the locking mechanism can be performed manually or via inhalation.

For manual resetting the latch 202 can comprise a tab 205. The tab can extend from a backing plate 206. The tab 205 can be arranged such that a force on the tab moves the latch 202 from a locked position to an unlocked position. For clarification, the latch 202 is arranged such that a force applied at an edge 206 can move the latch from position A, locked, to position B, unlocked. The force could be applied by a user, such as a user's finger.

For inhalation resetting the latch 202 can be arranged such that inhalation on the dry powder inhaler can cause the latch 202 to be moved from a locked position A to an unlocked position B. This is ideal as the latch 202 can thus be unlocked after a single dose of medicament has been inhaled. The latch 202 can be positioned at an air inlet 110 on the upper proximal reservoir housing 103.

Figure 5:
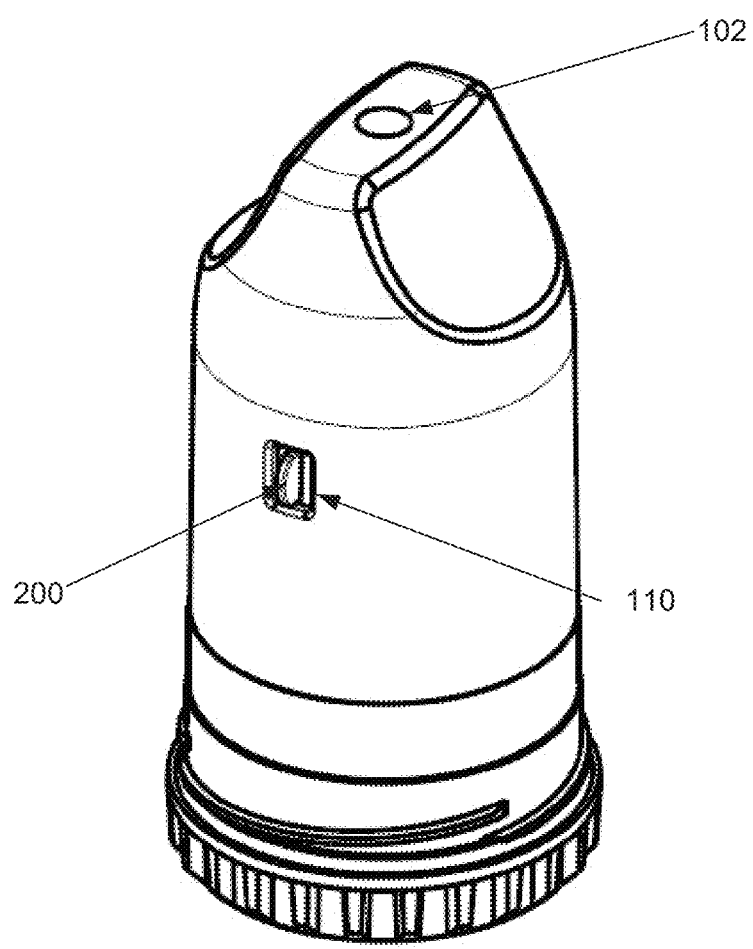
FIG. 5 is a perspective view of the dry powder inhaler showing a positioning of the locking mechanism at an air inlet.

FIG. 5 shows a view of the dry powder inhaler and one positioning of the locking mechanism such that inhalation can reset the latch 202. On inhalation at the air outlet 102 a general low pressure region is formed inside the dry powder inhaler 100. The low pressure region forms a pressure differential between the region inside the dry powder inhaler 100 and the region external to the dry powder inhaler 100; the pressure inside the dry powder inhaler being lower than the external pressure. The pressure differential can create a force on the latch 202 at the air inlet 110 having a direction inwards. This inwardly directed force can cause the latch 202 to be moved from a locked position A to an unlocked position B. With such a system the latch is unlocked after a single dose of medicament is inhaled.

Figure 6A:
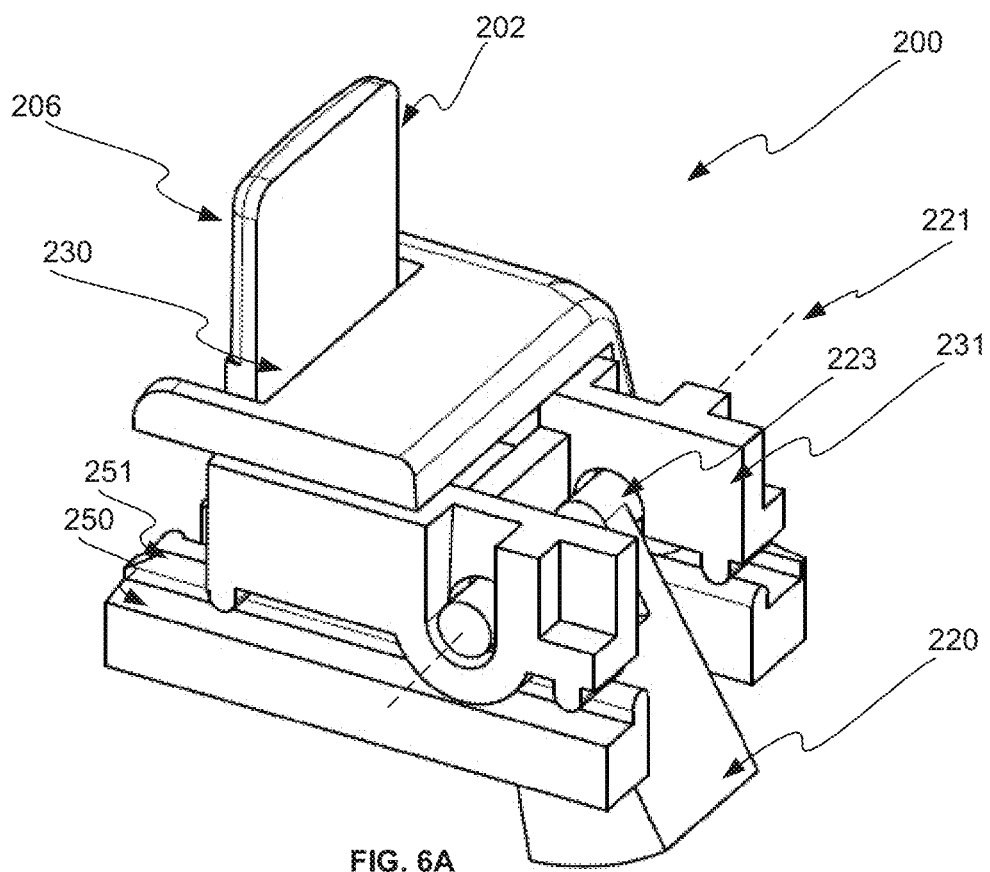
FIG. 6a is a perspective view of a locking mechanism having a pivotable counterweight.

FIGS. 6A and B clearly show the latch 202. The latch 202 can be carriage shaped as shown in FIG. 6. The latch 202 can slide along a track having a raised section 251 and an adjacent lowered section 250 provided in, for example, the supporting disc 204. The track can comprise a lowered section 250 between two raised sections 251 such that the two raised sections 251 form walls defining a channel. The sections are parallel and extend in a linear path from which extends radially from the centre of the dry powder inhaler. The latch 202 can be positioned at the track such that the lowered section 250 of the track can receive a fixed lateral member 252 of the latch 202. The latch 202 can be positioned such that the fixed lateral member 252 can also abut the raised section 251 of the track. As described above the latch 202 slides or moves along the track in a linear path which extends radially from the centre of the dry powder inhaler.

The latch 202 can be further provided with a planar face 306 extending perpendicular the perimeter of outer region 330 of the latch 202.

FIGS. 6A and B show a locking mechanism 200 in association with a pivotable counterweight 220. The counterweight 220 inhibits the outward movement of the latch 202. Due to the counterweight 220 the locking mechanism 200 cannot be inadvertently moved to a locking position. The latch 202 can generally only be moved to an outer position by being engaged by the guiding members 210 of the locking disc 201. For example, a user cannot inadvertently shake the dry powder inhaler such that the latch 202 is moved to an outer position.

Figure 6B:
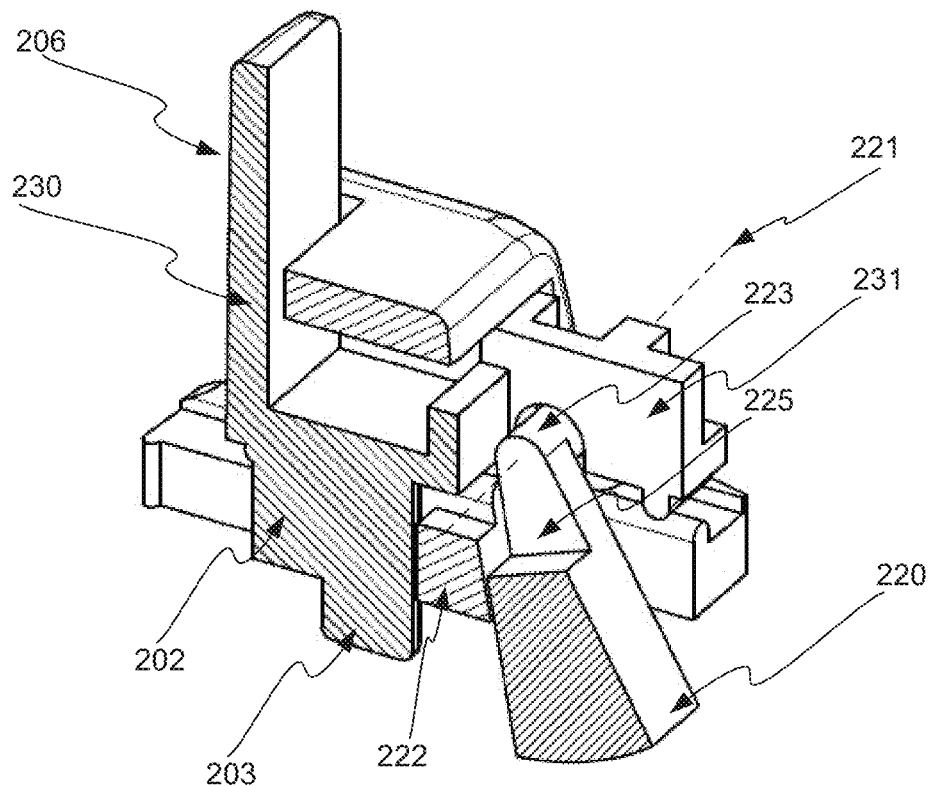
FIG. 6b is a cross sectional perspective view of a locking mechanism having a pivotable counterweight.

The pivotable counterweight 220 is pivotable around an axis 221. As is shown in FIG. 6 the axis 221 can be perpendicular to the direction of travel of the latch 202. As shown in FIG. 6B the axis is positioned such that the pivotable counterweight can have a mass at a distance from the axis 221 and rest against a stop 222 provided between the outermost face of the latch 202 and the counterweight 220. In such a system when the inhaler is held vertically upright force on the mass acts downwards and thus applies a force in the direction of the stop 222. Without the application of any external forces, such as forces from the guiding members 210, the counterweight is at rest and the stop 222 provides an equal force in the opposite direction such that the latch will not move outwards. The mass of the counterweight 220 acts to hold the latch in an inner position.

The latch 202 can be carriage formed as is shown in FIG. 6 and slide on the supporting disc 204.

As is seen in FIG. 6 the pivotable counterweight 220 extends from the pivoting axis 221 toward the longitudinal axis of the dry powder medicament inhaler 100.

The pivotable counterweight 220 is associated with a stop 222 such that the mass of the counterweight acts on the stop 222 to inhibit the outward movement of the incorrect dose prevention mechanism 300. The stop 222 can be provided between the outermost face 306 of the visual indicator 202 and the counterweight 220. In the embodiment shown in FIG. 6 the stop 222 is provided in the supporting disc 304.

The stop 222 can be declined with respect to the longitudinal axis of the inhaler. As can be seen in FIG. 6 when the inhaler is held vertically upright force on the mass acts downwards and due to the declination of the stop a force is generated inwardly, to prevent the latch 202 from moving to an outer position. The stop 222 does not need to be declined. If the stop 222 is not declined and is aligned with the longitudinal axis of the inhaler then a force inwards is generated in reaction to the application of any force tending to move the latch 202 outwards.

Figure 7A:
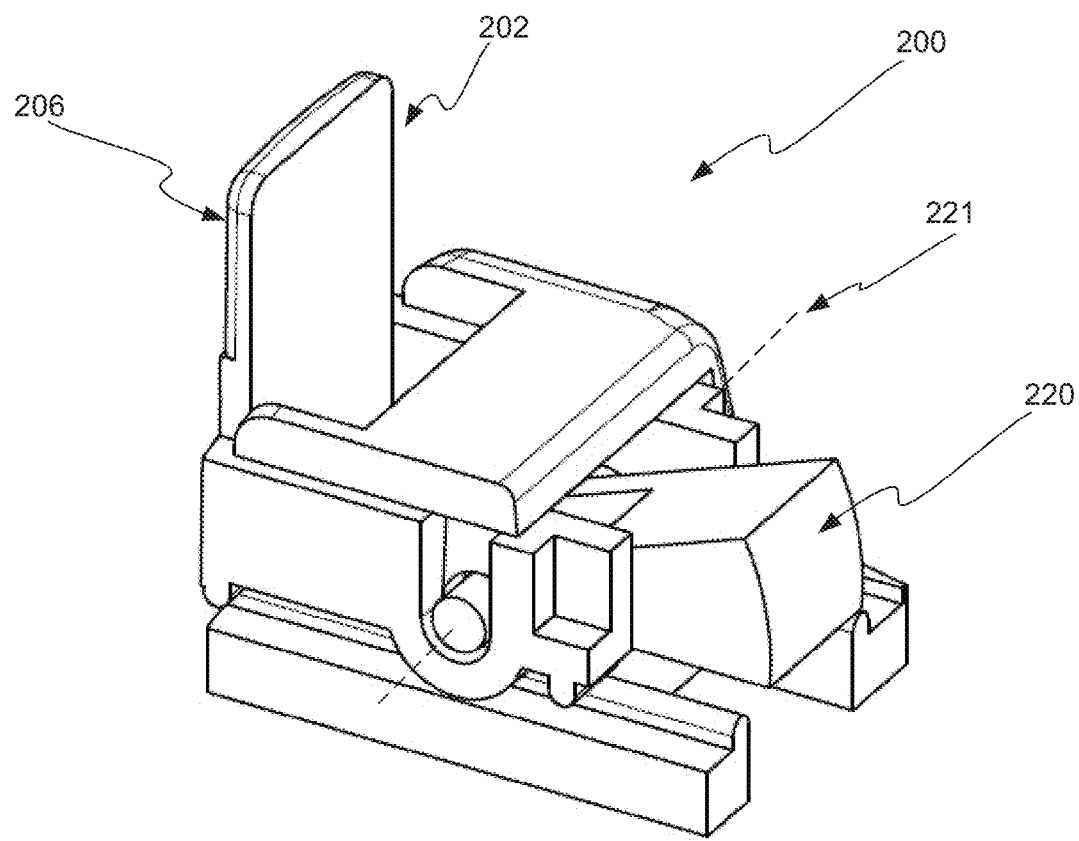
FIG. 7a is a perspective view of a locking mechanism having a pivotable counterweight being in an outward position.
Figure 7B:
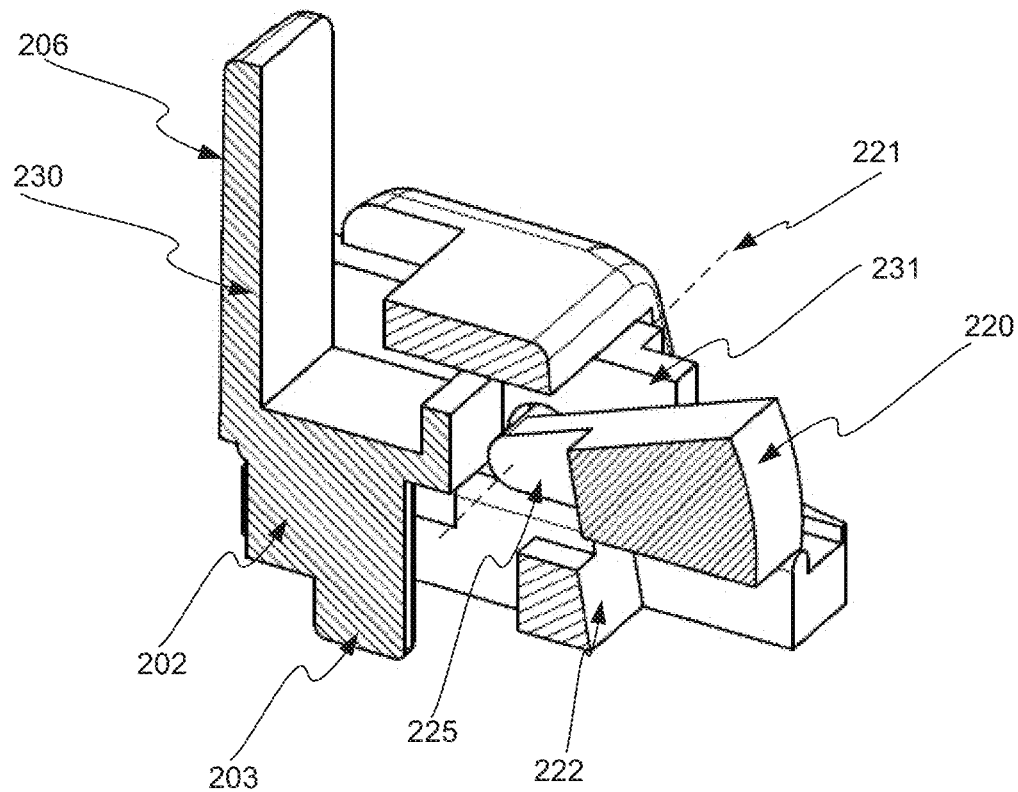
FIG. 7b is a cross sectional perspective view of a locking mechanism having a pivotable counterweight being in an outward position.

The pivotable counterweight 220 is dimensioned such that the centre of mass of the pivotable counterweight 220 is distal to the pivoting axis. As can be seen in FIGS. 5 to 7 one way to achieve this is to form a wedge shaped counterweight 220 where the thinner component of the wedge forms the proximal side connecting to the pivoting axis. The distal component is the thicker part of the wedge. The pivotable counterweight 220 can also be provided with a rounded edge at the distal end such that the number of corners is reduced.

The pivotable counterweight 220 can be connected to the latch 202 via at least one pin at the pivoting axis 221. As is shown in FIGS. 6-8 the pivotable counterweight 220 can be connected to the latch 202 via two pins 223 extending aligned with the pivoting axis 221. The pins can be insertable into recesses on the latch 202. The pivotable counterweight 220 can be provided with a recess 225 between the pins 223 such that the counterweight can be more easily inserted in to the recesses on the latch.

The backing plate 206 of the latch is positioned at an outer region such that it is externally visible.

On moving the latch 202 outwards then the pivotable counterweight 220 is made to pivot upwards against the downward acting force of gravity. As can be seen in FIGS. 7A and B, when the latch 202 is an outer, active, preventing position the counterweight rests in a substantially horizontal position. When resting in a horizontal position the counterweight 220 does not apply a force to the latch in an inwards direction. In this way the pivotable counterweight can apply a force only at the start, or during the movement of the locking mechanism. The pivotable counterweight does not provide an inwards force when the locking mechanism is in a preventing position.

Figure 8A:
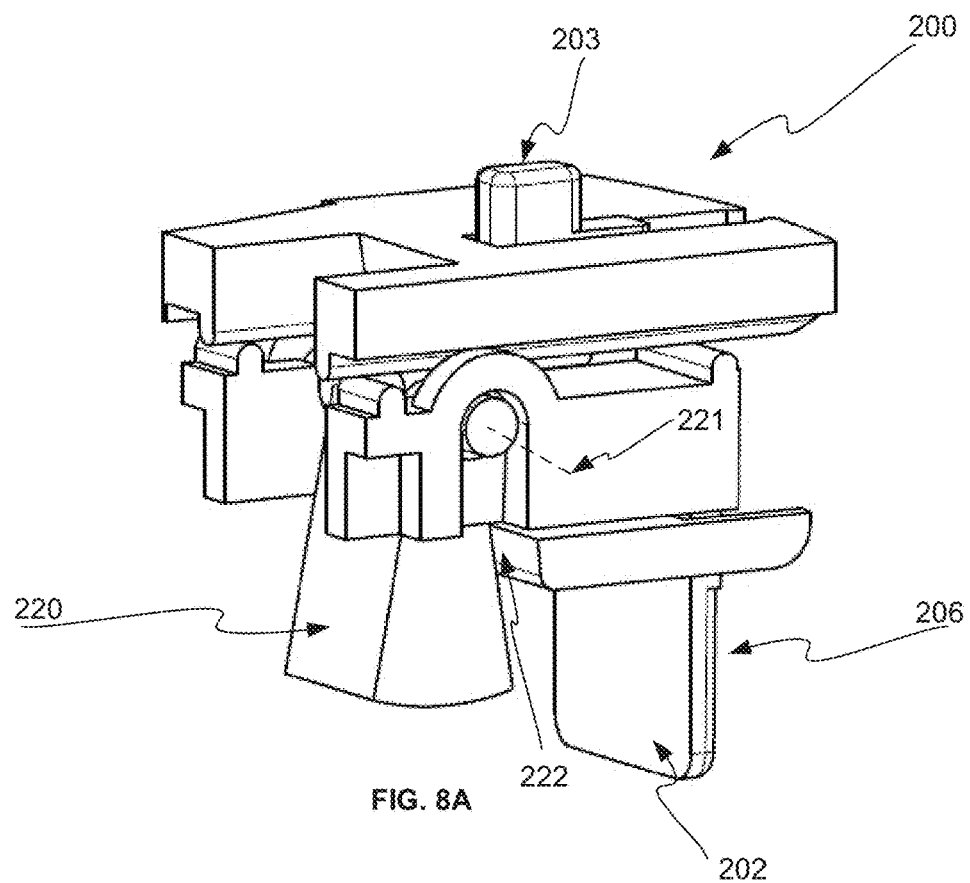
FIG. 8a is a perspective view of a visual indicator having a pivotable counterweight in an inverted position.
Figure 8B:
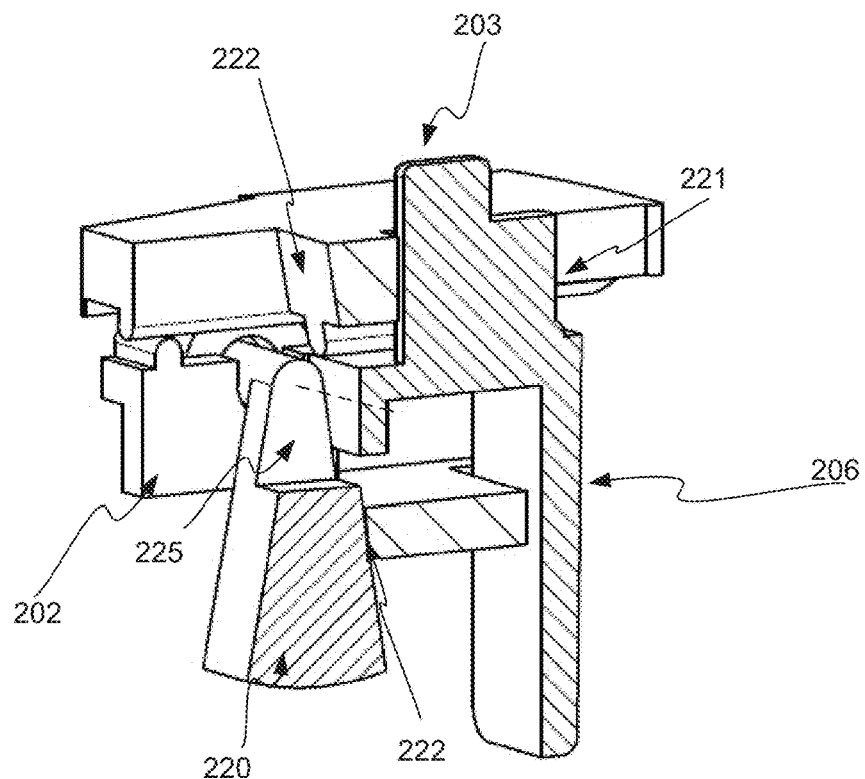
FIG. 8b is a cross sectional perspective view of a visual indicator having a pivotable counterweight in an inverted position.

As shown in FIGS. 8A and B if the dry powder inhaler 100 is inverted the counterweight continues to function and inhibit the latch 202 from moving outwards.

The different parts of the dry powder inhaler 100 may be manufactured in a suitable material, such as injection moldable plastics, such as thermoplastics.

Dry Powder Inhaler Comprising a Dosage Indicator—FIGS. 9 to 16

The following description of another embodiment of the present invention describes a dry powder inhaler comprising an indicator mechanism in association with a dose disk preventing the metering of medicament via the dose disk prior to inhalation of any previously metered medicament. The indicator mechanism can simultaneously be a locking mechanism as described above with reference to FIGS. 1 to 8.

Figure 9A:
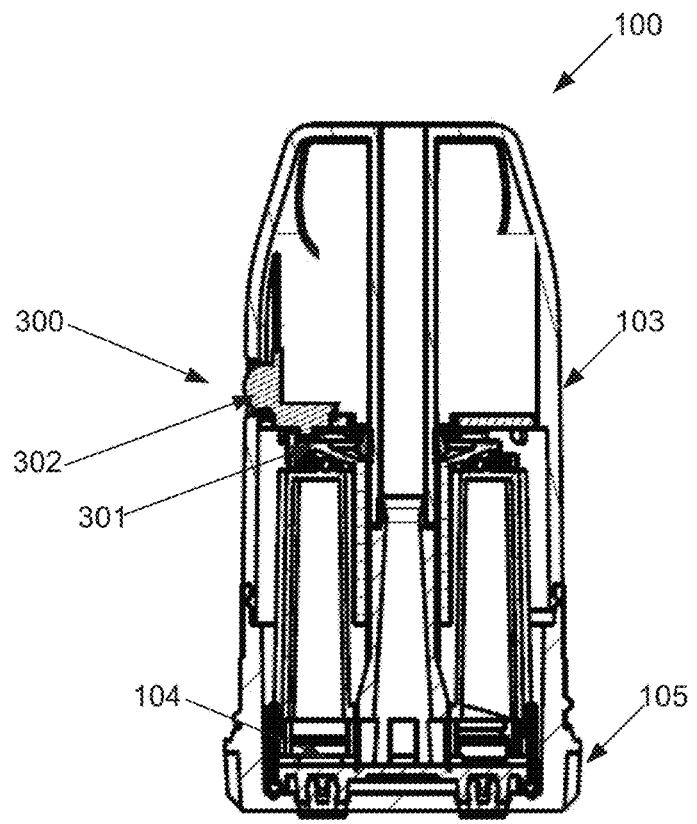
FIG. 9a is a perspective and cross-sectional view of the dry powder inhaler according to an embodiment of the second aspect of the invention.
Figure 9B:
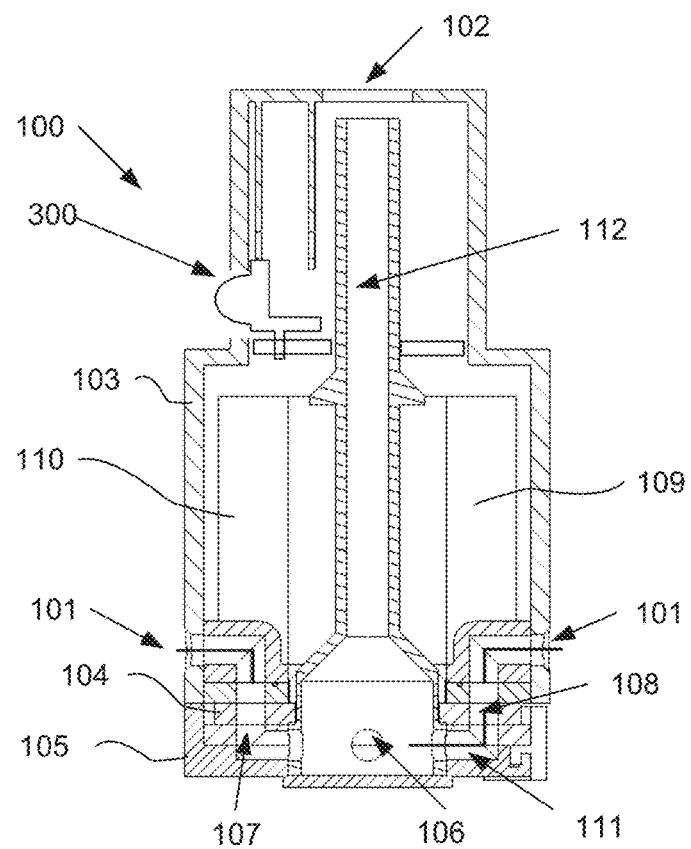
FIG. 9b is a perspective and cross-sectional view of the dry powder inhaler more clearly showing the inlets, outlet, and reservoirs.

FIGS. 9A and 9B illustrate a dry powder medicament inhaler 100 comprising an indicator mechanism 300 for restricting dose metering to a single dose. The dry powder medicament inhaler 100 comprises air inlets 101 and an air outlet 102. The outlet 102 is arranged at a first end of the dry powder drug inhaler 100, while the inlets 101 are arranged at a zone in an opposite second end of the dry powder drug inhaler 100. The outlet 102 is arranged centrally, along the longitudinal axis of the dry powder medicament inhaler 100. The inlets 101 may be arranged at a radial, in relation to the longitudinal axis of the dry powder drug inhaler 100, periphery of the dry powder inhaler 100, such that the inlets 101 lead inhaled air transversally and radially towards the central portion of the dry powder inhaler 100.

The dry powder medicament inhaler 100 comprises an upper proximal reservoir housing 103, a dose disc 104, and a lower distal twister 105. The reservoir housing 103 and the twister 105 cooperate so as to house the dose disc 104 in between these two. The twister 105 cooperates with the dose disc 104, such that the dose disc 104 may be rotated, via rotation and twisting of the twister 105, between a dose administering position and a dose collecting position. This may be accomplished by interconnecting the dose disc 104 and the twister 105 via interconnecting grooves and ribs, or letting the twister 105 extend longitudinally centrally of the dose disc 104 and connected thereto, such as disclosed for example in FIG. 9A. Preferably, the rotation of the dose disc 104 has two end positions, corresponding to the dose administering position and the dose collecting position, in its relation with the reservoir housing 103, in a known manner.

In the dose administering position, the inlets 101 are in fluid communication with a mixing and deaggregation chamber 106 via dosage communications 107. The dosage communications 107 then run through openings 108 in the dose disc 104. Hence, the openings 108, in the dose administering position, is superimposed the communications 107.

When rotating the dose disc 104 into a dose collecting position, the openings 108 are rotated away from fluid communication with the inlets 101 and the chamber 106. Instead, the openings 108 are rotated into medicament reservoirs 109, 110, wherein the openings 108 may collect a medicament housed in the reservoirs 109, 110. The medicament contained in the medicament reservoir 109 may be a medicament different from the medicament contained in the medicament reservoir 110. Due to the two reservoirs 109, 110, the inhaler 100 may deliver two substances in one inhalation, said two substances otherwise being incompatible, meaning that these two substances not would be possible to be comprised in one joint reservoir, such that a dry powder inhaler device 100 in which effective and satisfactory dispersion of the dry powder is obtained, which inhaler 100 can administer medicament comprising substances which can be incompatible in mixture or for other reasons are preferred to have in separate reservoirs 109,110.

It is possible to arrange the dose disc 104 and the openings 108 thereof such that when a first set of two openings 108 are superimposed the communications 107, i.e. in a dose administering position, a second set of two openings 108 are positioned in the medicament reservoirs 109, 110, respectively. Additionally, the distribution of the openings 108 on the dose disc 104 is such that the dose disc may be rotated in one direction only, which means that when the second set of two openings 108 are superimposed the communications 107, the first set of openings 108 are positioned in the medicament reservoirs 109, 110, respectively.

The dose disc 104 and the openings in the dose disc 108 in combination are hereafter referred to as the dosage mechanism 104, 108.

As the dosage mechanism 104, 108 of the dry powder medicament inhaler 100 is moved from a dose collecting position to a dose administering position the dosage indicator 300 indicates that a dose is ready to be inhaled.

The dosage indicator 300 is arranged in association with the dosage mechanism 104, 108 such that the dosage indicator 300 indicates that the dosage mechanism 104, 108 has administered a dose into the dose metering reservoirs 109, 110.

The dosage indicator 300 is arranged to have 2 states, an indicating state, indicating a dose is ready to be inhaled, or in a non-indicating state, indicating there is no dose ready to be inhaled. Clearly, the dosage indicator 300 could also be arranged such that in an indicating state, the dosage indicator indicates that a dose has been successfully inhaled, or that there is no dose present, and in a non-indicating state, the indicator indicates that a dose is ready to be inhaled.

The dosage indicator 300 helps the user to avoid the inadvertent metering of multiple doses in to dose metering reservoirs 109,110 as the user has an indication and/or feedback of whether or not a dose has been metered into the dose metering reservoirs 109, 11.

Figure 10A:
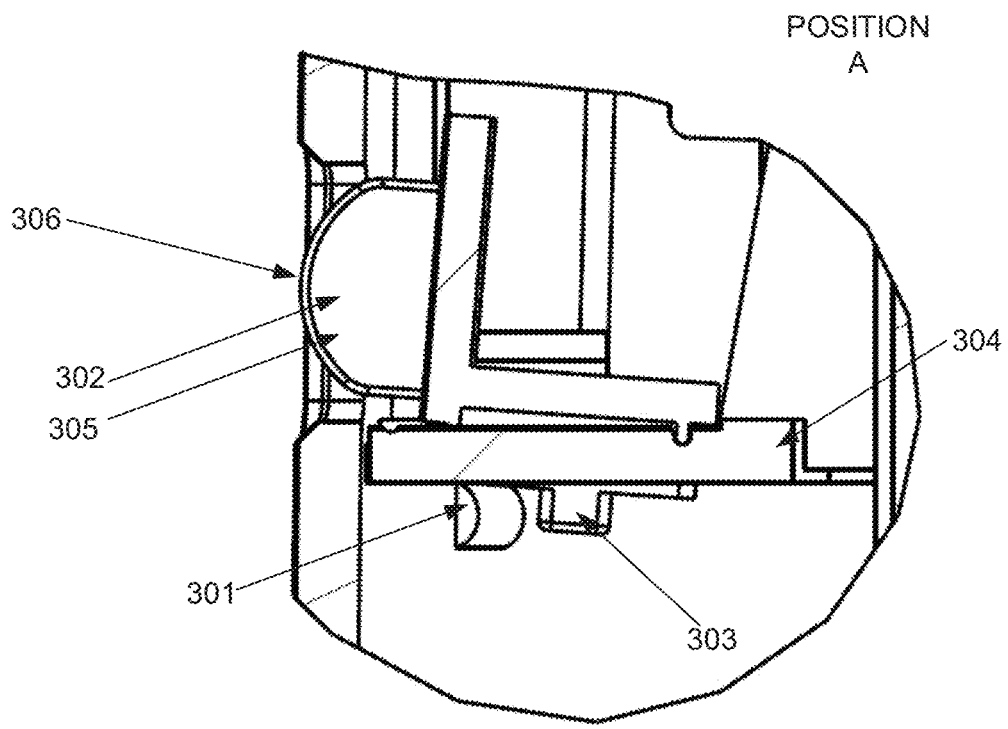
FIG. 10a is a perspective and cut-away view of an indicator mechanism according to one embodiment of the present invention.
Figure 10B:
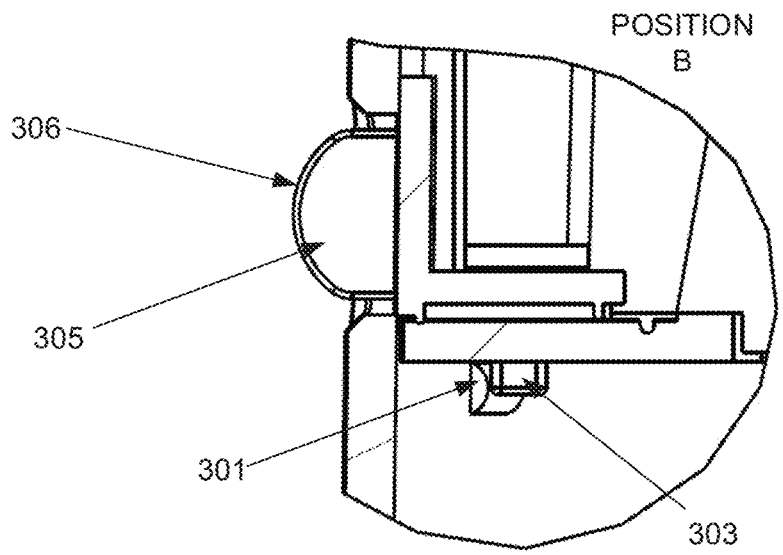
FIG. 10b is a perspective and cut-away view of the indicator mechanism according to one embodiment of the present invention.

As shown in FIGS. 10A and 10B the dosage indicator 300 comprises a visual indicator 302 arranged in association with a rotating disc 301. The rotating disc 301 is a disc having an axis of rotation aligned with the longitudinal axis of the dry powder medicament inhaler 100. The visual indicator 302 can be arranged such that it can form the two states of the dosage indicator 300. The visual indicator 302 is thus provided with two states, a first state, indicating state in which there is an indication that a dose has been metered into the dose metering reservoirs and is ready for inhalation and a second, non-indicating state, in which there is no indication and there is no dose ready for inhalation as the previous dose has been inhaled, or a dose is yet to be metered.

One way of constructing the visual indicator 302 such that it can be moved mechanically from a first indicating state to a second, non-indicating state is described hereafter.

The visual indicator 302 can be moved radially inwards towards a central longitudinal axis of the dry powder medicament inhaler to move to a non-indicating position and then can be moved radially outwards to move to an indicating position. As opposed to the rotation of the rotating disc 301 the visual indicator 302 moves along in a substantially linear path. The linear path may be a radial line extending from the central longitudinal axis of the dry powder inhaler outwardly perpendicular to the longitudinal axis. However, it is enough that the linear path is directed inwardly, and not necessarily to cross the central longitudinal axis of the inhaler 100, such that the indicator is withdrawn into the inhaler 100. The visual indicator 302 can be arranged above the rotating disc 301. A substantially flat supporting disc 304 can be located between the visual indicator 302 and the rotating disc 301. The supporting disc 304 acts as a guide and a support for the visual indicator 302.

Figure 14A:
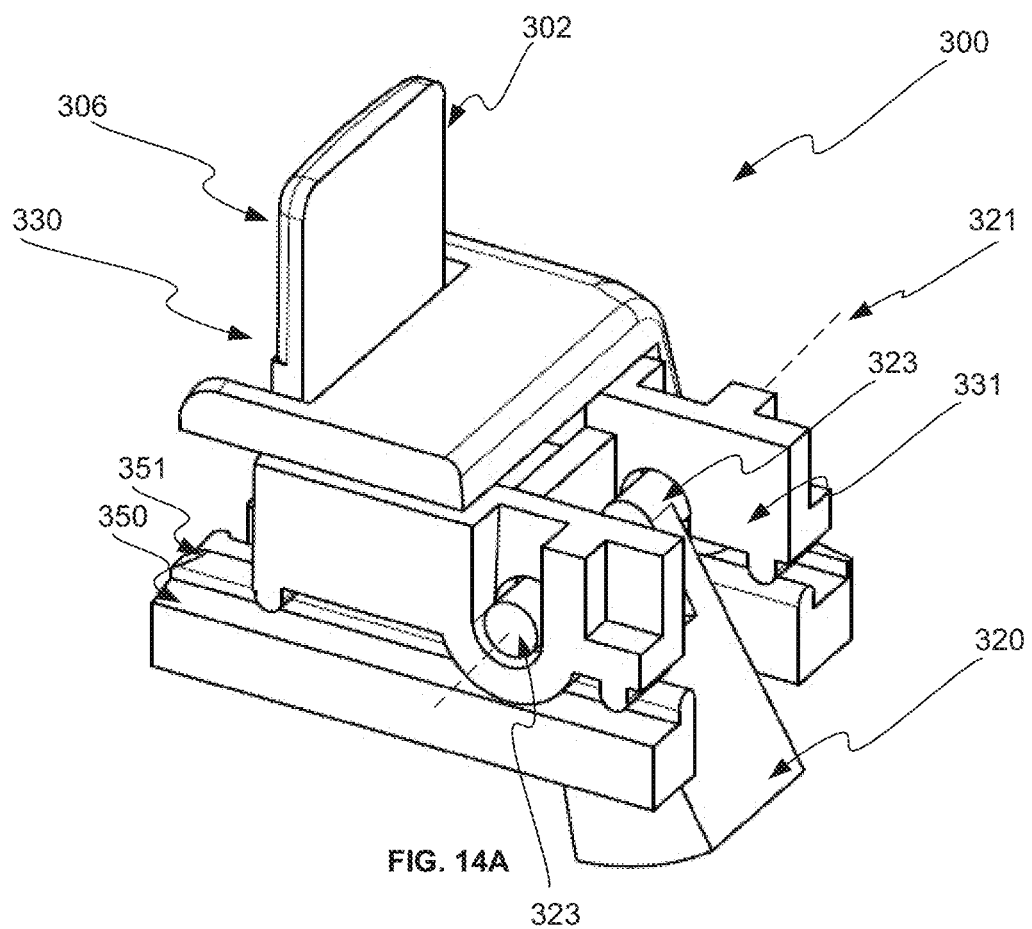
FIG. 14a is a perspective view of a visual indicator having a pivotable counterweight.

For visual indication the visual indicator 302 can comprise a tab 305. The tab can extend from a backing plate 306. The tab can extend through an opening in the upper proximal reservoir housing. For enhanced visual feedback the tab can further be coloured in a different colour to the colour of the proximal reservoir housing. A tab extending through an opening in the upper proximal reservoir housing and could also provide tactile indication in combination with visual indication. This visual indicator does not need to have a tab but could, as shown in FIGS. 14A and B, comprise a backing plate 306 which acts as the visual indicator.

Figure 13A:
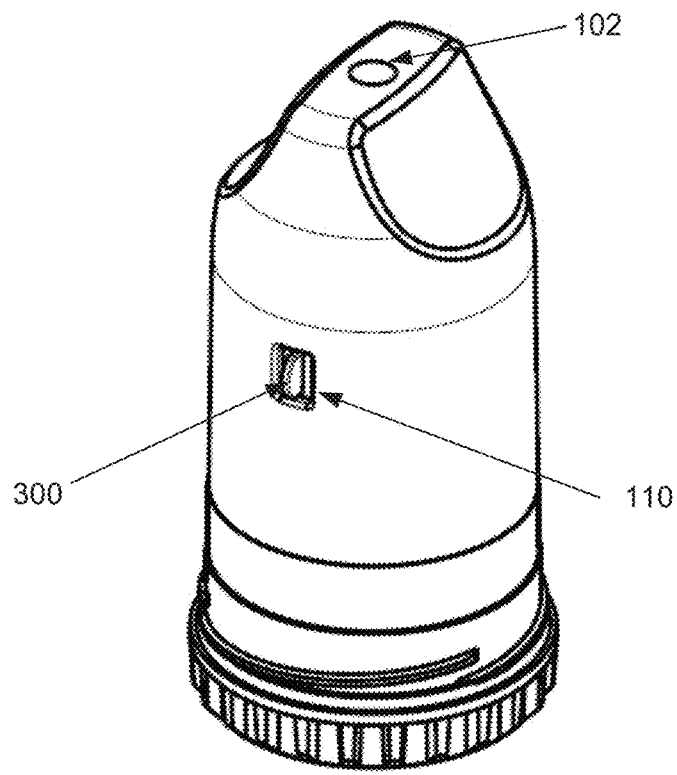
FIG. 13a is a perspective view of the dry powder inhaler showing a positioning of the dosage indicator at an air inlet.
Figure 13B:
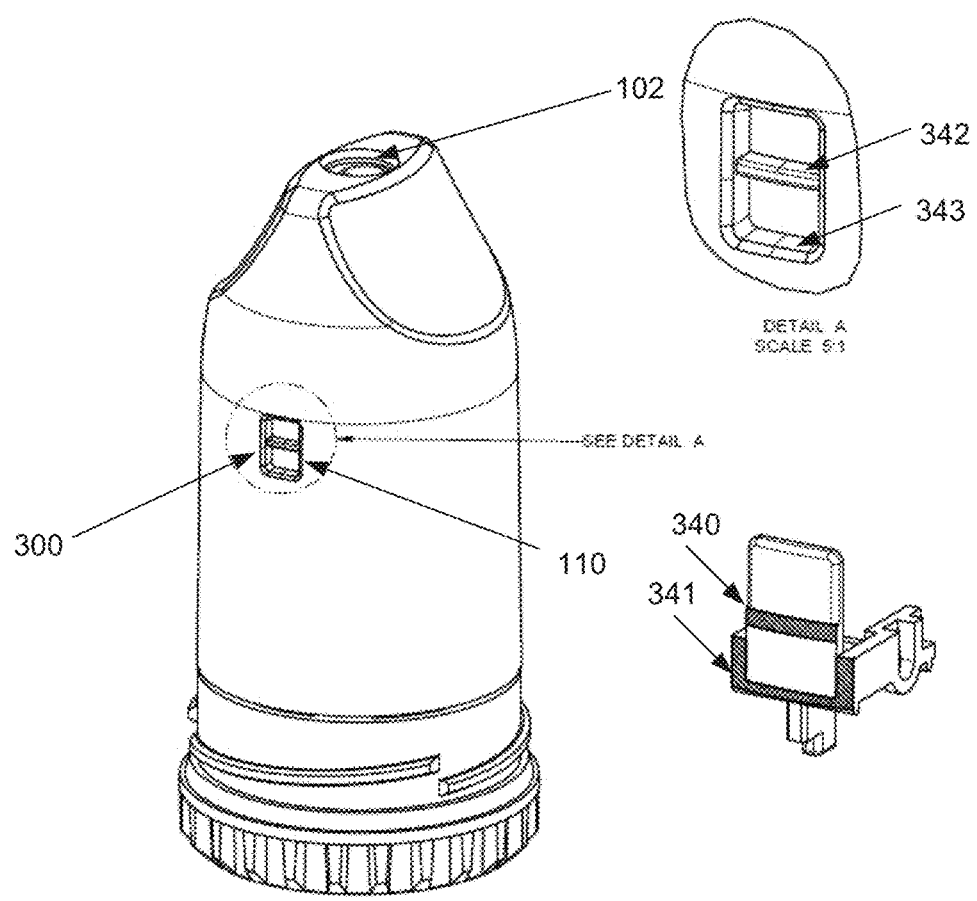
FIG. 13b is a perspective view of the dry powder inhaler showing a positioning of the dosage indicator having a highly visible coloured band.

FIG. 13B shows a dosage indicator a highly visible coloured band 340. The band can be coloured in a highly visible signalling colour. The coloured band 340 is positioned on the planar face 306 of the sliding component 302. As shown in FIG. 13B the perimeter of the outer region of the sliding component 341 can be provided with a highly visible coloured region. If a coloured region is provided on the face of the sliding component and/or on the surrounding region then the coloured region can be obscured by a beam 342 at the air inlet 110 and by the edge 341 of the air-inlet 110 in a first position, for example, the sliding component being in an outer position. In a second position, there can be a separation between the sliding component and the beam 342 and the edge 341 such that the coloured region is visible. In this way the incorrect dose prevention mechanism is a dosage indicator.

The visual indicator 302 could also be formed at an opening in the upper proximal reservoir but not extend through the opening. In such a form the visual indicator 302 comprises a first part having a first visual appearance, and a second visually distinctive part. For example, the first part could be the same colour as the upper proximal reservoir housing whilst the second part is coloured differently. On moving the indicator from a first non-indicating state to a second indicating state the visually distinctive part becomes visible.

The rotating disc 301 is associated with the dose disc 104 and twister 105 such that rotation of the dose disc 104 or twister 105 causes rotation of the rotating disc 301. The dose disc 104 and the rotating disc 301 are arranged substantially parallel and have aligned central axes.

The dose disc 104 and the rotating disc 301 can be fixed upon a central shaft. The shaft may be sleeve formed and be arranged on the outside of an inhalation chimney 112. Fixing the rotating disc 301 and the dose disc 104 to a central shaft means that the dose disc 104 and the rotating disc 301 are locked in their rotation. The dose disc 104 and the rotating disc 301 may also be associated by other means such that rotation in one disc causes a rotation in the other.

Figure 11A:
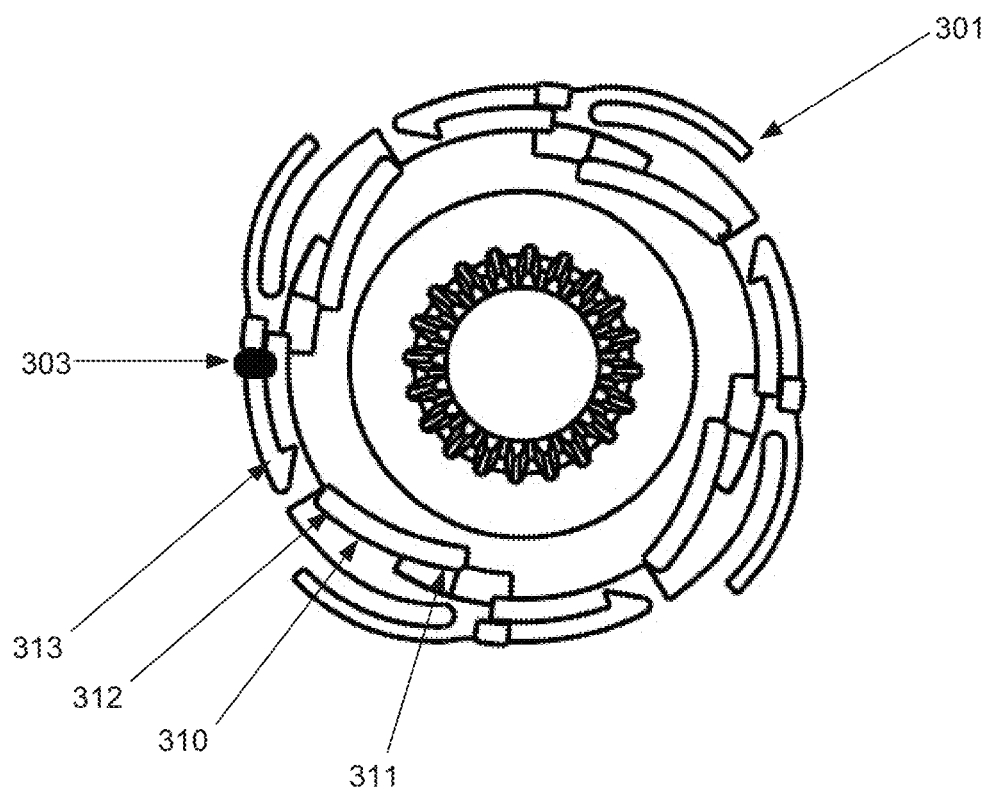
FIG. 11a is a top-down exploded view of the locking disc of the indicator mechanism according to one embodiment of the present invention.
Figure 11B:
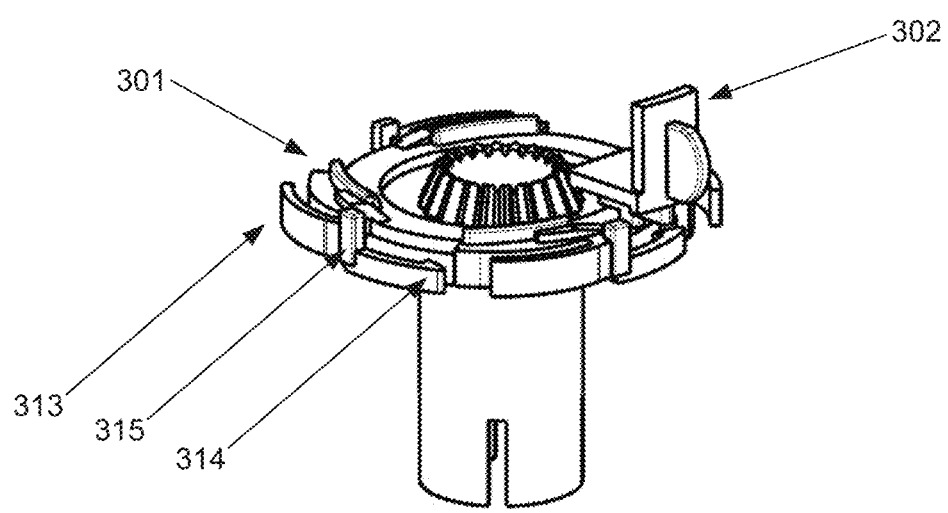
FIG. 11b is a perspective exploded view of the locking disc and latch of the indicator mechanism according to one embodiment of the present invention.

The rotating disc 301 is shown in FIG. 11. The rotating disc comprises guiding members 310 extending at an angle from the circumference of the rotating disc 301. The guiding members extend in a plane parallel and aligned with the plane formed by the locking disc 301. The guiding members 310 are arranged such that they are closer to the centre of the rotating disc 301 at a first end 311 than at a second end 312.

Figure 12A:
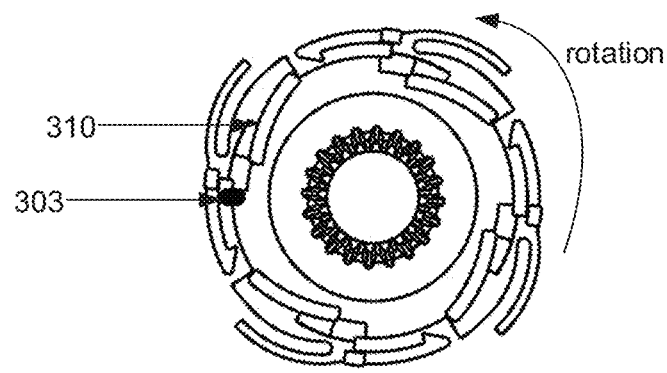
FIGS. 12a-12e are cross sectional exploded views of the dosage indicator focusing on the indicator and guiding disc during different points of rotation of the guiding disc.
Figure 12B:
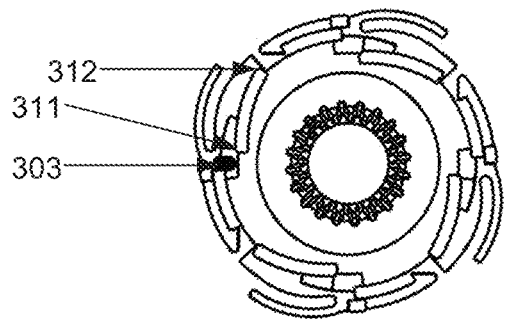
Figure 12C:
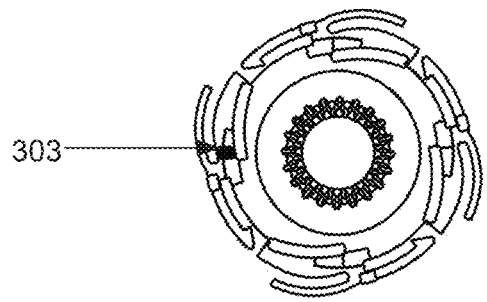
Figure 12D:
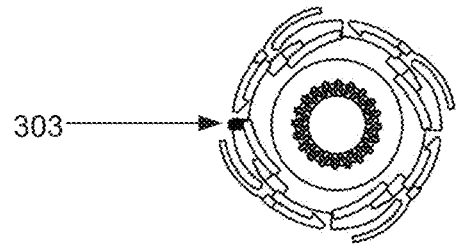
Figure 12E:
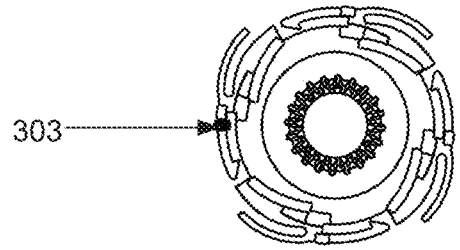

The indicator being in a non-indicating position is shown in a top down view in FIG. 12A, wherein a projection 303 from visual indicator 302 does not interfere with members of the rotating disc 301. As the dose disc 104 is rotated the rotating disc 301 is also rotated. The first end 311 of the guiding members, being closer to the centre of the locking disc 301, contacts the projection 303 as shown in FIG. 12B. As the dose disc is further rotated the rotating disc 301 rotates further and the projection 303 slides along the length of the guiding member 310 towards the second end 312 as shown in FIG. 12C. As the second end 312 of the guiding member 310 is further from the centre of the rotating disc, during rotation of the dose disc 104 and the rotating disc 301 the projection 303 and the indicator 302 are moved outwardly from the centre of the rotating disc 301 as shown in FIG. 12D.

During rotation of the dose disc 104 the dose disc moves from a dose collecting position to a dose administering position.

To set the indicator to a non-indicating state from an indicating state is called resetting the dosage indicator.

For inhalation resetting the indicator 302 can be arranged such that inhalation on the dry powder inhaler can cause the indicator 302 to be moved from an indicating position to a non-indicating position. The indicator can be positioned at an air inlet 110 on the upper proximal reservoir housing 103. This is ideal as the indicator 302 can thus be reset after a single dose of medicament has been inhaled.

FIGS. 13A and 13B show a view of the dry powder inhaler and one positioning of the dosage indicator such that inhalation can reset the indicator 302. On inhalation at the air outlet 102 a general low pressure region is formed inside the dry powder inhaler 100. The low pressure region forms a pressure differential between the region inside the dry powder inhaler 100 and the region external to the dry powder inhaler 100; the pressure inside the dry powder inhaler being lower than the external pressure. The pressure differential can create a force on the indicator 302 at the air inlet 110 having a direction inwards. This inwardly directed force can cause the indicator 302 to be moved from an indicating state to an non-indicating state. With such a system the indicator is reset after a single dose of medicament is inhaled.

For visual indication the indicator 302 could also comprise a light which illuminates when the indicator is in an indicating state. The light may be positioned on the upper proximal housing 103. As the light does not need to be mechanically connected to the rotating disc 301 as a mechanical indicator would the light can be positioned in a variety of locations on the upper proximal housing and does not necessarily need to be positioned at the air-inlet 110.

Figure 14B:
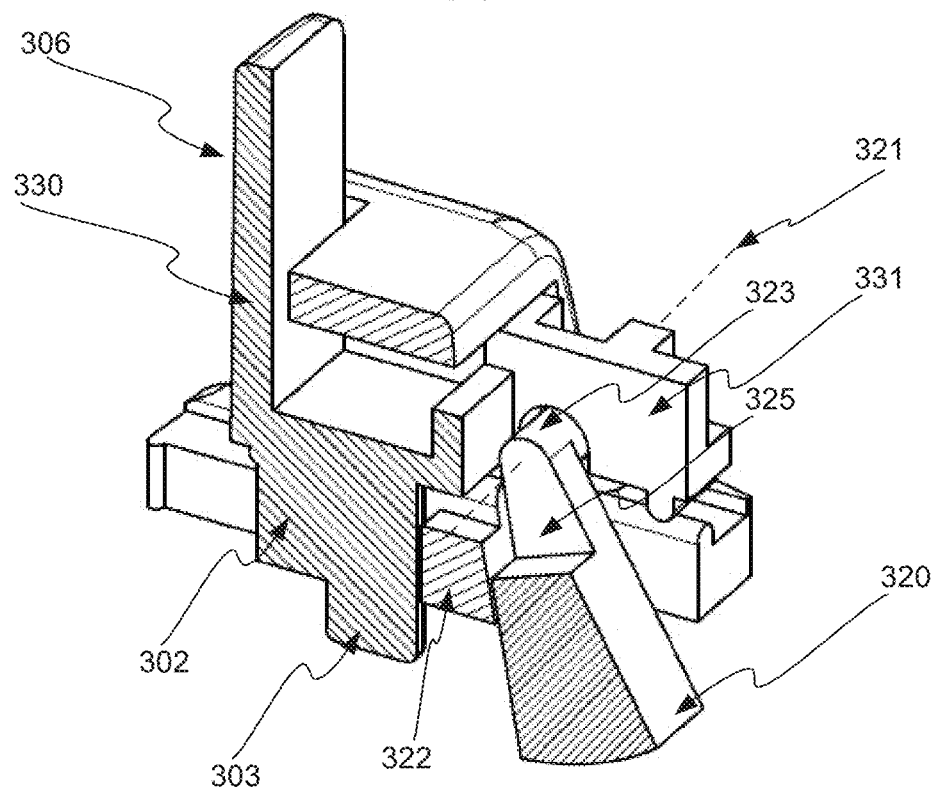
FIG. 14b is a cross sectional perspective view of a visual indicator having a pivotable counterweight.

FIGS. 14A and 14B clearly show the visual indicator 302. The visual indicator 302 can be carriage shaped as shown in FIGS. 14A and 14B. The visual indicator can slide along a track having a raised section 351 and an adjacent lowered section 350 provided in, for example, the supporting disc 304. The track can comprise a lowered section 350 between two raised sections 351 such that the two raised sections 351 form walls defining a channel. The sections are parallel and extend in a linear path from which extends radially from the centre of the dry powder inhaler. The visual indicator 302 can be positioned at the track such that the lowered section 350 of the track can receive a fixed lateral member 352 of the visual indicator. The visual indicator can be positioned such that the fixed lateral member 352 can also abut the raised section 351 of the track. As described above the visual indicator slides or moves along the track in a linear path which extends radially from the centre of the dry powder inhaler.

The visual indicator can be further provided with a planar face 306 extending perpendicular the perimeter of outer region 330 of the visual indicator 302.

FIGS. 14A and 14B show a dosage indicator 300 in association with a pivotable counterweight 320. The counterweight 320 inhibits the outward movement of the visual indicator 302. Due to the counterweight 320 the dosage indicator 300 cannot be inadvertently moved to an indicating position. The visual indicator 302 can generally only be moved to an outer position by being engaged by the guiding members 310 of the locking disc 301. For example, a user cannot inadvertently shake the dry powder inhaler such that the visual indicator 302 is moved to an outer position.

The pivotable counterweight 320 is pivotable around an axis 321. As is shown in FIG. 14A the axis 321 can be perpendicular to the direction of travel of the visual indicator 302. As shown in FIG. 14B the axis is positioned such that the pivotable counterweight can have a mass at a distance from the axis 321 and rest against a stop 322 provided between the outermost face of the visual indicator 302 and the counterweight 320. In such a system when the inhaler is held vertically upright force on the mass acts downwards and thus applies a force in the direction of the stop 322. Without the application of any external forces, such as forces from the guiding members 310, the counterweight is at rest and the stop 322 provides an equal force in the opposite direction such that the visual indicator will not move outwards. The mass of the counterweight 320 acts to hold the visual indicator in an inner position.

The visual indicator 302 can be carriage formed as is shown in FIGS. 14A and 14B and slide on the supporting disc 304.

As is seen in FIGS. 14A and 14B the pivotable counterweight 320 extends from the pivoting axis 321 toward the longitudinal axis of the dry powder medicament inhaler 100.

The pivotable counterweight 320 is associated with a stop 322 such that the mass of the counterweight acts on the stop 322 to inhibit the outward movement of the incorrect dose prevention mechanism 300. The stop 322 can be provided between the outermost face 306 of the visual indicator 302 and the counterweight 320. In the embodiment shown in FIG. 14 the stop 322 is provided in the supporting disc 304.

The stop 322 can be declined with respect to the longitudinal axis of the inhaler. As can be seen in FIG. 14 when the inhaler is held vertically upright force on the mass acts downwards and due to the declination of the stop a force is generated inwardly, to prevent the visual indicator 302 from moving to an outer position. The stop 322 does not need to be declined. If the stop 322 is not declined and is aligned with the longitudinal axis of the inhaler then a force inwards is generated in reaction to the application of any force tending to move the visual indicator 302 outwards.

The pivotable counterweight 320 is dimensioned such that the centre of mass of the pivotable counterweight 320 is distal to the pivoting axis. As can be seen in FIGS. 13 to 15 one way to achieve this is to form a wedge shaped counterweight 320 where the thinner component of the wedge forms the proximal side connecting to the pivoting axis. The distal component is the thicker part of the wedge. The pivotable counterweight 320 can also be provided with a rounded edge at the distal end such that the number of corners is reduced.

The pivotable counterweight 320 can be connected to the visual indicator 302 via at least one pin at the pivoting axis 321. As is shown in FIGS. 14 to 16 the pivotable counterweight 320 can be connected to the visual indicator 302 via two pins 323 extending aligned with the pivoting axis 321. The pins can be insertable into recesses on the visual indicator 302. The pivotable counterweight 320 can be provided with a recess 325 between the pins 323 such that the counterweight can be more easily inserted in to the recesses on the visual indicator.

The backing plate 306 of the visual indicator is positioned at an outer region such that it is externally visible.

Figure 15A:
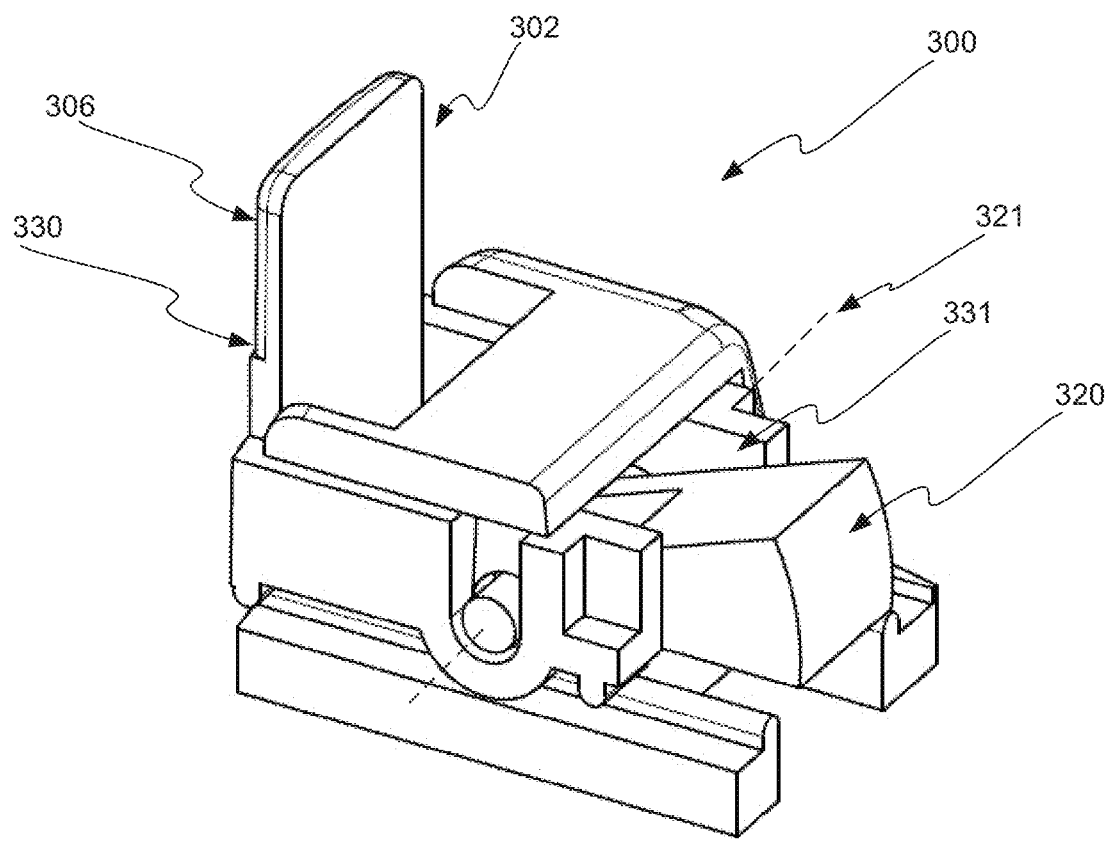
FIG. 15a is a perspective view of a visual indicator having a pivotable counterweight being in an outward position.
Figure 15B:
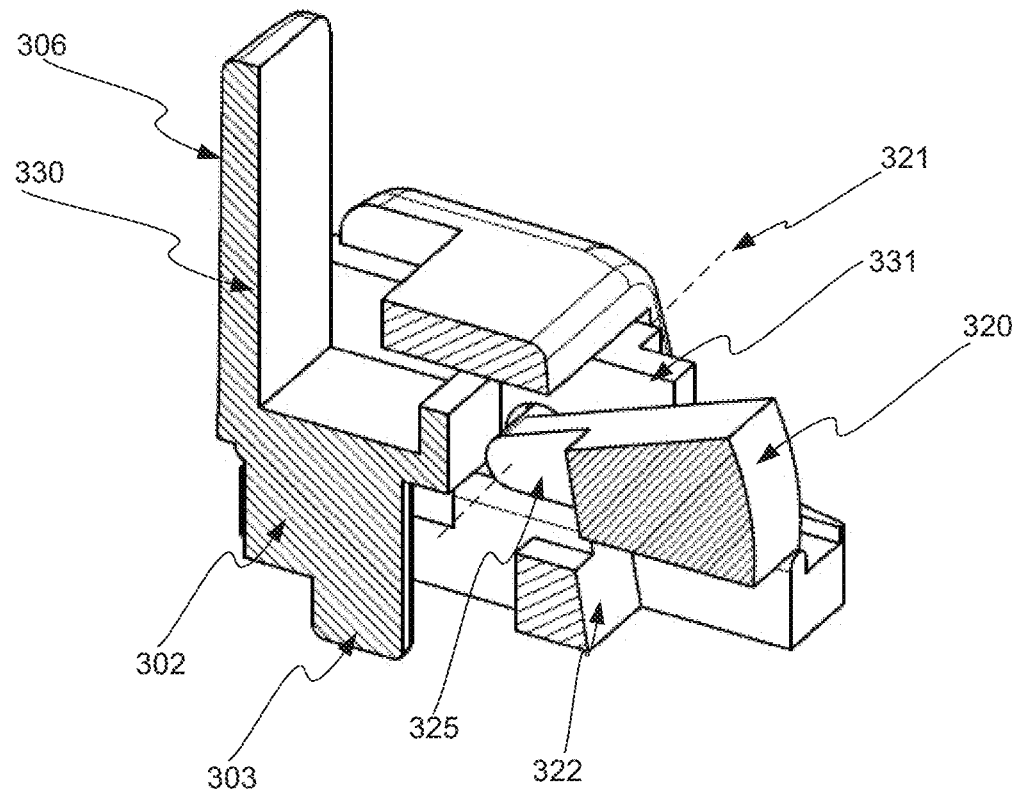
FIG. 15b is a cross sectional perspective view of a visual indicator having a pivotable counterweight being in an outward position.

On moving the visual indicator 302 outwards then the pivotable counterweight 320 is made to pivot upwards against the downward acting force of gravity. As can be seen in FIGS. 15A and 15B, when the visual indicator 302 is an outer, indicating position the counterweight rests in a substantially horizontal position. When resting in a horizontal position the counterweight 320 does not apply a force to the visual indicator in an inwards direction. In this way the pivotable counterweight can apply a force generally only at the start, or during the movement of the dosage indicator, not when it is an outer position. The pivotable counterweight does not provide an inwards force when the dosage indicator 300 is in a preventing position.

Figure 16A:
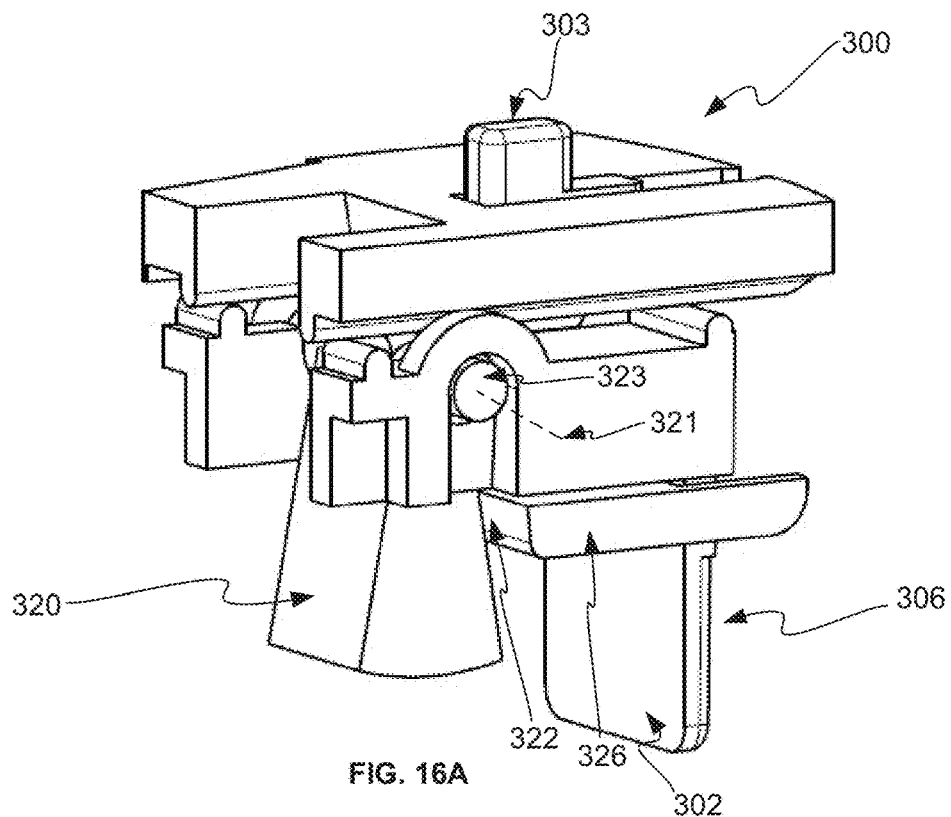
FIG. 16a is a perspective view of a visual indicator having a pivotable counterweight in an inverted position.
Figure 16B:
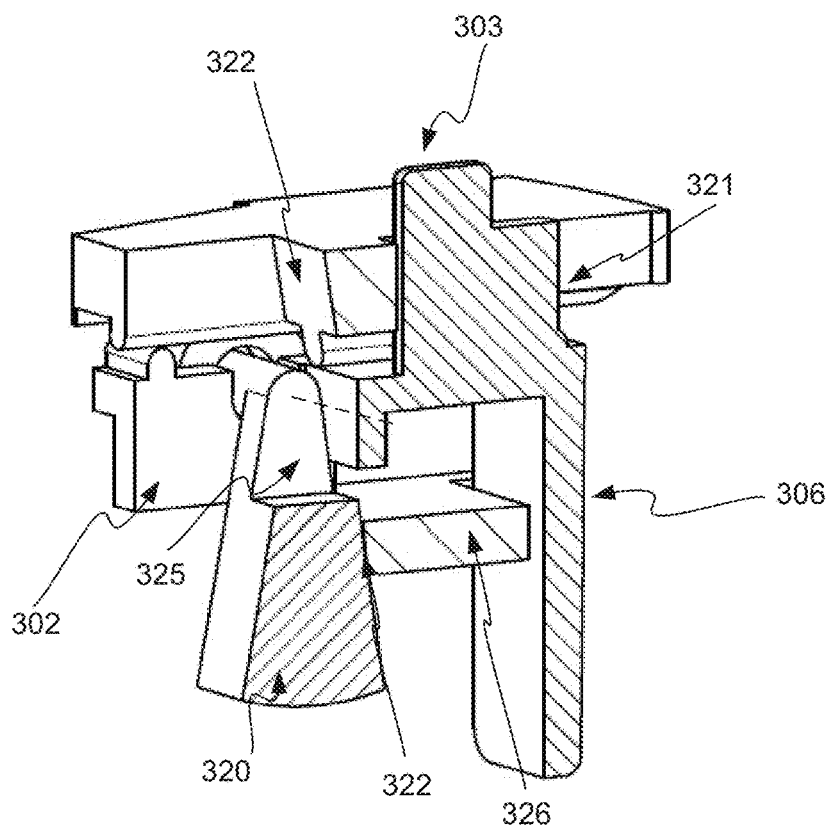
FIG. 16b is a cross sectional perspective view of a visual indicator having a pivotable counterweight in an inverted position.

As shown in FIGS. 16A and 16B if the dry powder inhaler 100 is inverted the counterweight continues to function and inhibit the visual indicator 302 from moving outwards. FIG. 10 shows a dry powder medicament inhaler wherein the dosage indicator further acts as a locking mechanism 300 as was described above in respect of the embodiment in FIGS. 1 to 8. The combined indicating and locking mechanism 300 functions such that on moving the dosage mechanism 104, 108 from a dose collecting position to a dose administering position the mechanism 300 is moved from an unlocked and non-indicating position to a locked and indicating position preventing the metering of any further doses prior to resetting of the locking mechanism.

The locking mechanism 300 can restrict the inadvertent metering of multiple doses in to dose metering reservoirs 109,110 as the locking mechanism must be unlocked prior to metering a new dose into the dose metering reservoirs 109,110. The locking mechanism can also restrict the intentional misuse of the inhaler by requiring the inhalation of a previously metered dose prior to metering any new dose.

As shown in FIG. 10 the locking mechanism 300 comprises a guiding disc, which, when the dosage indicator is also a locking mechanism, can be called a locking disc 301 and a combined indicator and latch 302. The combined indicator and latch 302 is provided with two end positions being an outer locked position A and an inner unlocked position B.

The combined indicator and latch 302 is associated with the locking disc 301 such that a projection 303 from the indicator and latch 302 can, in a locked position A, extend through a plane of the locking disc 301 and be aligned such that it is possible that the projection 303 abuts a member or members of the locking disc 301. One way of achieving this is that the indicator and latch 302 can be moved radially inwards towards a central longitudinal axis of the dry powder medicament inhaler to move to an unlocked position and then can be moved radially outwards to move to a locked position. In a locked position A, the combined and indicator latch 302 is in an indicating position. Whereas, in an unlocked position, B, the combined indicator and latch 302 is not in an indicating position.

In an unlocked position B, the projection 303 from the indicator and latch 302 can also extend through the plane of the locking disc 301 but in an unlocked position the indicator and latch 302 does not abut the member or members of the locking disc 301 such that the locking disc 301 can be rotated. One way of achieving this is that the projection 303 of the indicator and latch 302 in a locked position A is aligned with circumferential members of the locking disc 301 whereas in an unlocked position B the projection 303 of the indicator and latch 302 is out of alignment with the circumferential members of the locking disc such that the locking disc 301 can be rotated. For example, the circumferential members could be the vertical stops 315 disclosed in FIG. 11B.

When the combined indicator and latch 302 is in position A the locking disc 301 cannot rotate and thus the dose disc 104 cannot rotate. When the latch is in position B the locking disc 301 and the dose disc 104 can both rotate.

When the guiding disc is a locking disc 301 it further comprises peripheral locking members 313. The peripheral locking members 313 extend from the circumference of the locking disc 301. The peripheral locking members 313 have a base 314 extending parallel to the plane of the locking disc 301 and a vertical stops 315 extending perpendicular to the plane of the locking disc 301. The vertical stop extends 315 substantially vertically. The peripheral locking members 313 are positioned at a distance further from the centre of the locking disc 301 than the guiding members 310. The peripheral locking members are dimensioned such that the projection 303 of the combined indicator and latch 302 can act as a limit to stop any rotation 303 of the locking disc 301 and as they can be fixed to the same shaft, the dose disc 104.

As described above with respect to the inhaler in FIGS. 1 to 8, the different parts of the dry powder inhaler 100 may be manufactured in a suitable material, such as injection moldable plastics, such as thermoplastics.

Dry Powder Inhaler Comprising a Counterweight Mechanism—FIGS. 17 to 24

The following description of yet another embodiment of the present invention describes a dry powder medicament inhaler comprising an incorrect dose prevention mechanism comprising a counterweight in association with a dose disk preventing the incorrect metering of medicament by the user.

Figure 17A:
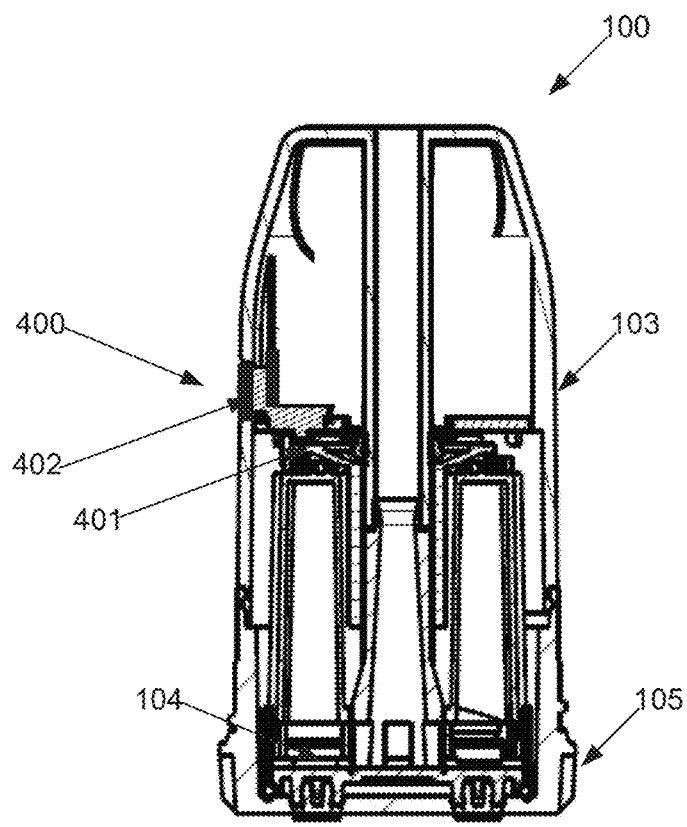
FIG. 17a is a perspective and cross-sectional view of a dry powder medicament inhaler not having a counterweight mechanism.
Figure 17B:
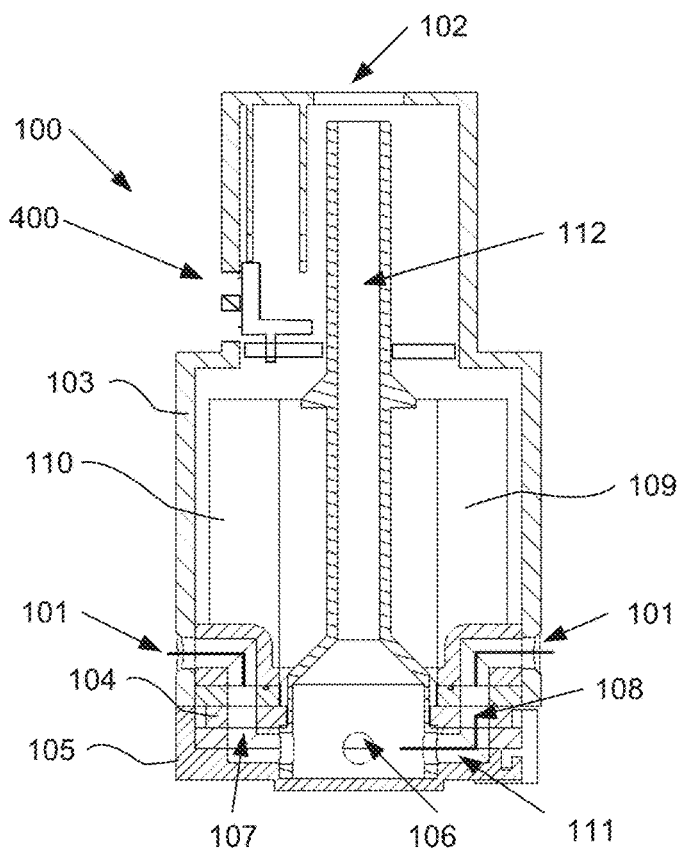
FIG. 17b is a perspective and cross-sectional view of the dry powder medicament inhaler not having a counterweight mechanism more clearly showing the inlets, outlet, and reservoirs.

FIGS. 17A and 17B illustrate a dry powder medicament inhaler 100 comprising an incorrect dose prevention mechanism 400 for preventing the incorrect metering of medicament by a user. The dry powder medicament inhaler 100 comprises air inlets 101 and an air outlet 102. The outlet 102 is arranged at a first end of the dry powder medicament inhaler 100, while the inlets 101 are arranged at a zone in an opposite second end of the dry powder drug inhaler 100. The outlet 102 is arranged centrally, along the longitudinal axis of the dry powder medicament inhaler 100. The inlets 101 may be arranged at a radial, in relation to the longitudinal axis of the dry powder drug inhaler 100, periphery of the dry powder medicament inhaler 100, such that the inlets 101 lead inhaled air transversally and radially towards the central portion of the dry powder medicament inhaler 100.

The dry powder medicament inhaler 100 comprises an upper proximal reservoir housing 103, a dose disc 104, and a lower distal twister 105. The reservoir housing 103 and the twister 105 cooperate so as to house the dose disc 104 in between these two. The twister 105 cooperates with the dose disc 104, such that the dose disc 104 may be rotated, via rotation and twisting of the twister 105, between a dose administering position and a dose collecting position. This may be accomplished by interconnecting the dose disc 104 and the twister 105 via interconnecting grooves and ribs, or letting the twister 105 extend longitudinally centrally of the dose disc 104 and connected thereto, such as disclosed for example in FIG. 17. Preferably, the rotation of the dose disc 104 has two end positions, corresponding to the dose administering position and the dose collecting position, in its relation with the reservoir housing 103, in a known manner.

In the dose administering position, the inlets 101 are in fluid communication with a mixing and deaggregation chamber 106 via dosage communications 107. The dosage communications 107 then run through openings 108 in the dose disc 104. Hence, the openings 108, in the dose administering position, are superimposed with the communications 107. When rotating the dose disc 104 into a dose collecting position, the openings 108 are rotated away from fluid communication with the inlets 101 and the chamber 106. Instead, the openings 108 are rotated into medicament reservoirs 109, 110, wherein the openings 108 may collect a medicament housed in the reservoirs 109, 110. The medicament contained in the medicament reservoir 109 may be a medicament different from the medicament contained in the medicament reservoir 110. Due to the two reservoirs 109, 110, the inhaler 100 may deliver two substances in one inhalation, said two substances otherwise being incompatible, meaning that these two substances not would be possible to be comprised in one joint reservoir, such that a dry powder medicament inhaler device 100 in which effective and satisfactory dispersion of the dry powder is obtained, which inhaler 100 can administer medicament comprising substances which can be incompatible in mixture or for other reasons are preferred to have in separate reservoirs 109,110.

It is possible to arrange the dose disc 104 and the openings 108 thereof such that when a first set of two openings 108 are superimposed the communications 107, i.e. in a dose administering position, a second set of two openings 108 are positioned in the medicament reservoirs 109, 110, respectively. Additionally, the distribution of the openings 108 on the dose disc 104 is such that the dose disc may be rotated in one direction only, which means that when the second set of two openings 108 are superimposed the communications 107, the first set of openings 108 are positioned in the medicament reservoirs 109, 110, respectively.

The dose disc 104 and the openings in the dose disc 108 in combination are hereafter referred to as the dosage mechanism 104, 108.

As the dosage mechanism 104, 108 of the dry powder medicament inhaler 100 is moved from a dose collecting position to a dose administering position the incorrect dose prevention mechanism 400 is activated and moved to an outer, preventing position.

The incorrect dose prevention mechanism 400 is arranged in cooperation with the dosage mechanism such that on moving the dosage mechanism 104, 108 from a dose collecting position to a dose administering position the incorrect dose prevention mechanism 400 is activated and moved to a preventing position.

The incorrect dose prevention mechanism 400 is arranged to have 2 states, an active, preventing state, generally outer state, wherein a dose is prevented from being metered, inactive, non-preventing, generally inner state, allowing a dose to be metered. The incorrect dose prevention mechanism can, for example, be a dose indicator mechanism. A dose indicator mechanism can indicate to the user of the dry powder medicament inhaler 100 that a dose is ready to be inhaled, or that a dose has been inhaled. The incorrect dose prevention mechanism 400 can also be a dose locking mechanism. A dose locking mechanism restricts the metering of a new dose prior to inhalation any previously metered doses. This can be performed by the dose locking mechanism restricting the movement of the dose-disc 104 and twister 105 after a dose has been metered.

The incorrect dose prevention mechanism can also be both a combined indicating and a locking mechanism. If the indicator is a combined indicator and locking mechanism then when a dose is ready to be inhaled the locking mechanism 400 prevents the metering of a new dose into the dose metering reservoirs 109, 110 as well as indicating in some way that a dose is ready to be inhaled. In this way the combined dose indicator and locking mechanism prevents the metering of incorrect doses into the dose metering reservoirs 109, 110.

Figure 18A:
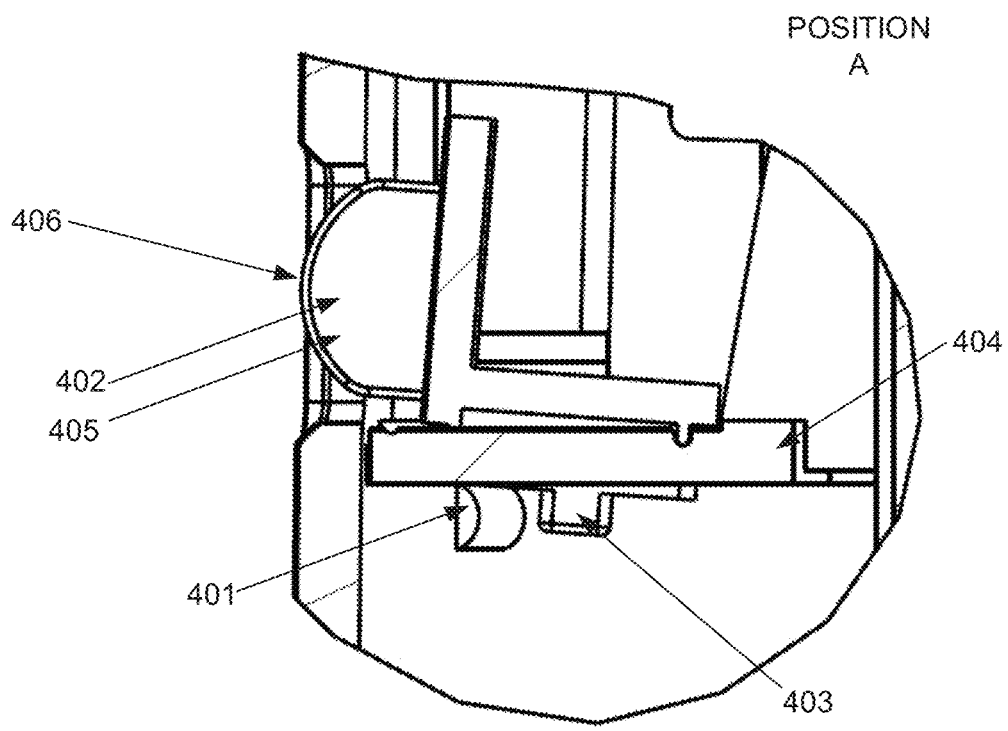
FIG. 18a is a perspective and cut-away view of an incorrect dose prevention mechanism not having a counterweight in an un-locked position.
Figure 18B:
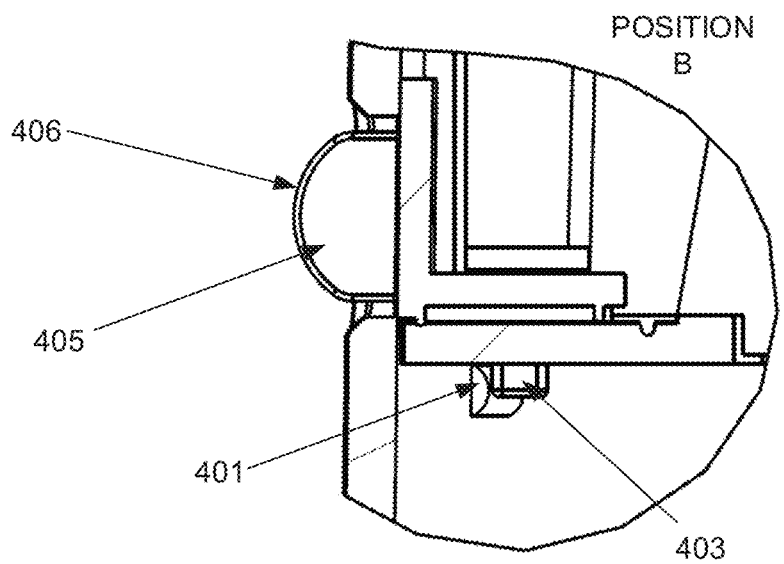
FIG. 18b is a perspective and cut-away view of the incorrect dose prevention mechanism, being a locking mechanism, not having a counterweight in a locked position.

FIGS. 18A and 18B show an incorrect dose prevention mechanism 400. The incorrect dose prevention mechanism 400 comprises a sliding component 402 arranged in association with a rotating disc 401. The rotating disc 401 is a disc having an axis of rotation aligned with the longitudinal axis of the dry powder medicament inhaler 100. The sliding component 402 can be arranged such that it can form the two states of the incorrect dose prevention mechanism 400.

One way of constructing the sliding component 402 such that it can be moved mechanically from a first inner, inactive, non preventing state to a second, active, outer, preventing state is described hereafter. The outer state of the sliding component can correspond to the active, preventing state of the incorrect dosage prevention mechanism 400. Accordingly, the inner state of the sliding component 402 can correspond to the inactive, non-preventing state of the incorrect dosage prevention mechanism 400.

Starting from an inner, inactive, non-preventing position or state the sliding component 402 can also be moved radially outwards to an outer, active, preventing position indicating that a dose is ready to be inhaled. The sliding component 402 moves along a substantially linear path. The linear path being a segment of a radial line extending from the longitudinal axis of the dry powder medicament inhaler outwardly perpendicular to the longitudinal axis. The sliding component 402 can be arranged above the rotating disc 401. A substantially flat supporting disc 404 can be located between the sliding component 402 and the rotating disc 401. The supporting disc 404 acts as a guide and a support for the sliding component 402.

To reset the incorrect dose prevention mechanism 400 and to allow a new dose to be metered the sliding component 402 can be moved radially inwards towards a longitudinal axis of the dry powder medicament inhaler to move to an inner, inactive, non-preventing position. In the inner, inactive, non-preventing position the sliding component does not prevent the metering of a new dose in to the dose metering reservoir.

To ensure that the incorrect dose prevention mechanism 400 is not moved to an undesirable state a pivotable counterweight 420 is associated with the incorrect dose prevention mechanism 400 such that the counterweight 420 inhibits the activation of the incorrect dose prevention mechanism. The inhibiting of activation can be performed by inhibiting the outward movement of the incorrect dose prevention mechanism.

It would be undesirable if the incorrect dose prevention mechanism could be moved to an outer, active, preventing state without a dose being metered. For example, if the user shook or inverted the dry powder medicament inhaler the incorrect dose prevention mechanism 400 should not be moved to an outer, active, preventing position. As can be seen in FIG. 22 to ensure that the incorrect dose prevention mechanism 400 is not moved to an undesirable state a pivotable counterweight 420 is associated with the incorrect dose prevention mechanism 400 such that the pivotable counterweight 420 inhibits the outward movement of the incorrect dose prevention mechanism 400.

The pivotable counterweight 420 acts to apply a force to the sliding component 402 in an inwards direction. That is, the counterweight generally applies a force having a component towards the longitudinal axis of the dry powder medicament inhaler 100. In this way this inwards acting force inhibits the outward movement of the incorrect dose prevention mechanism.

As can be seen in FIG. 22 the sliding component can be considered to have an outer region 430 and an inner region 431. The inner region is the region closest to the longitudinal axis of the dry powder medicament inhaler 100. The pivotable counterweight 420 pivots around a pivoting axis 421 the axis being positioned at the inner region 431 of the sliding component 402.

Figure 22A:
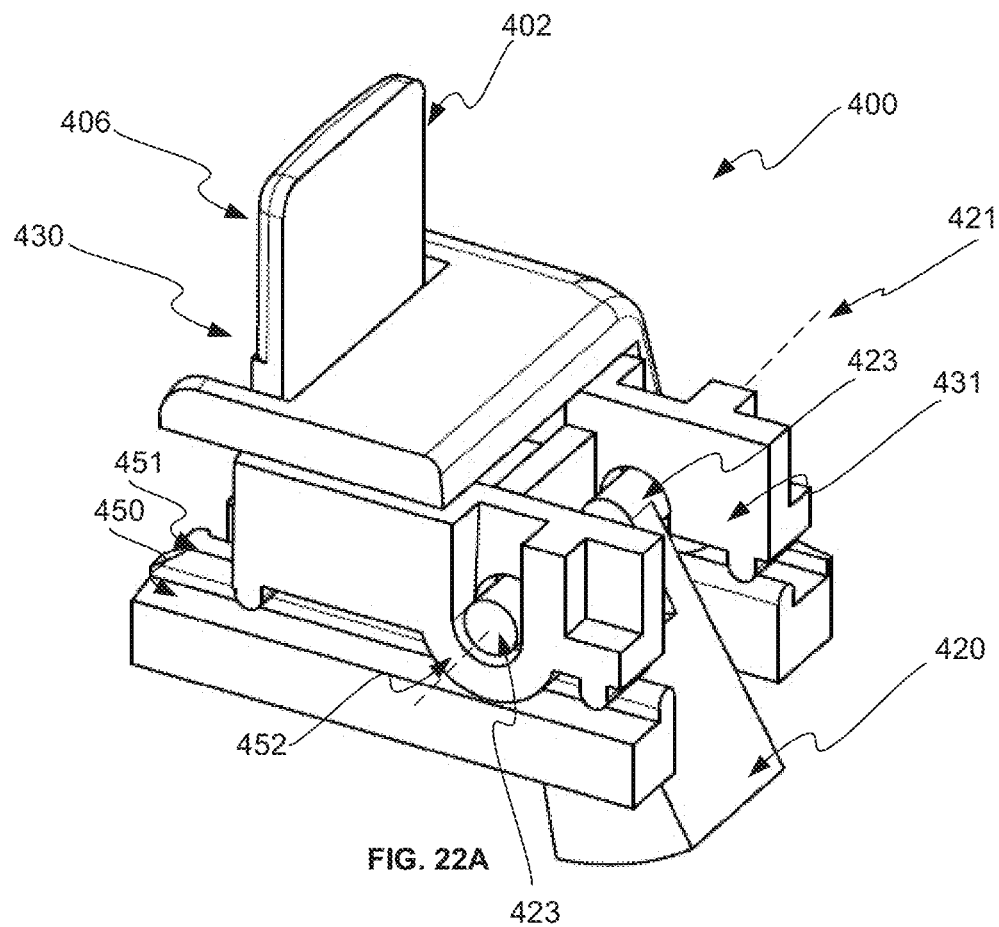
FIG. 22a is a perspective view of an incorrect dose prevention mechanism having a pivotable counterweight.
Figure 22B:
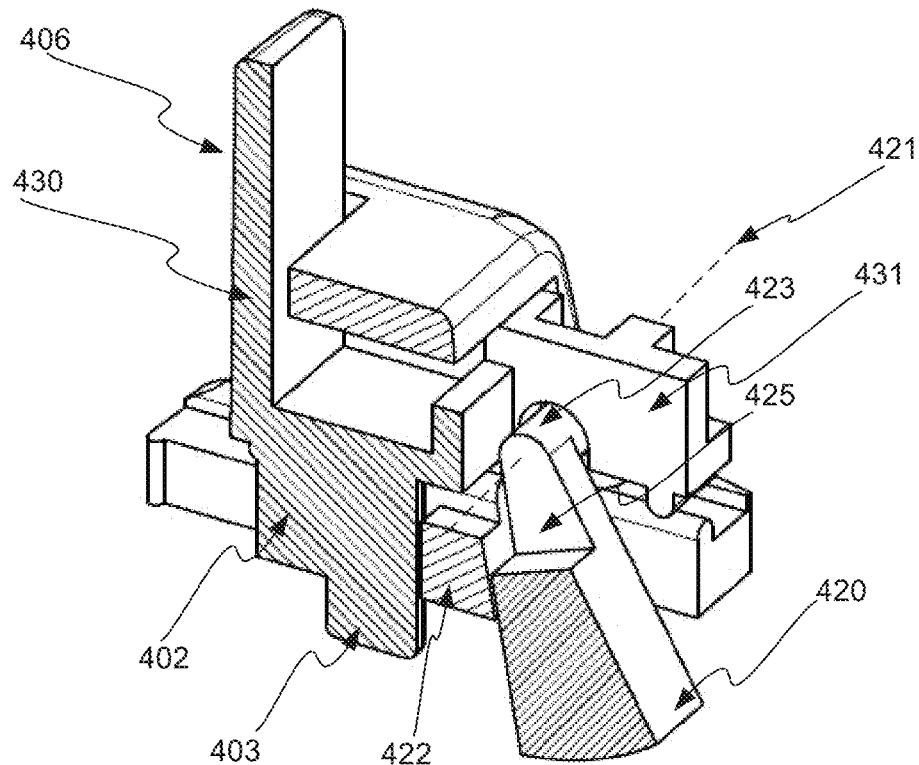
FIG. 22b is a cross sectional perspective view of an incorrect dose prevention mechanism having a pivotable counterweight.

FIGS. 22A and 22B clearly shows the sliding component 402. The sliding component 402 can be carriage shaped as shown in FIG. 22. The sliding component can slide along a track having a raised section 451 and an adjacent lowered section 450 provided in, for example, the supporting disc 404. The track can comprise a lowered section 450 between two raised sections 451 such that the two raised sections 451 form walls defining a channel. The sections are parallel and extend in a linear path from which extends radially from the centre of the dry powder inhaler. The sliding component 402 can be positioned at the track such that the lowered section 450 of the track can receive a fixed lateral member 452 of the sliding component. The sliding component can be positioned such that the fixed lateral member 452 can also abut the raised section 451 of the track. As described above the sliding component slides or moves along the track in a linear path which extends radially from the centre of the dry powder inhaler.

The sliding component can be further provided with a planar face 406 extending perpendicular the perimeter of outer region 430 of the sliding component 402.

As is seen in FIG. 22 the pivotable counterweight 420 extends from the pivoting axis 421 toward the longitudinal axis of the dry powder medicament inhaler 100.

The pivotable counterweight 420 is associated with a stop 422 such that the mass of the counterweight acts on the stop 422 to inhibit the outward movement of the incorrect dose prevention mechanism 400. The stop 422 can be provided between the outermost face 406 of the visual indicator 402 and the counterweight 420. In the embodiment shown in FIG. 22 the stop 422 is provided in the supporting disc 404.

The stop 422 can be declined with respect to the longitudinal axis of the inhaler. As can be seen in FIG. 22 when the inhaler is held vertically upright force on the mass acts downwards and due to the declination of the stop a force is generated inwardly, to prevent the sliding component 402 from moving to an outer position. The stop 422 does not need to be declined. If the stop 422 is not declined and is aligned with the longitudinal axis of the inhaler then a force inwards is generated in reaction to the application of any force tending to move the sliding component 402 outwards.

Figure 21:
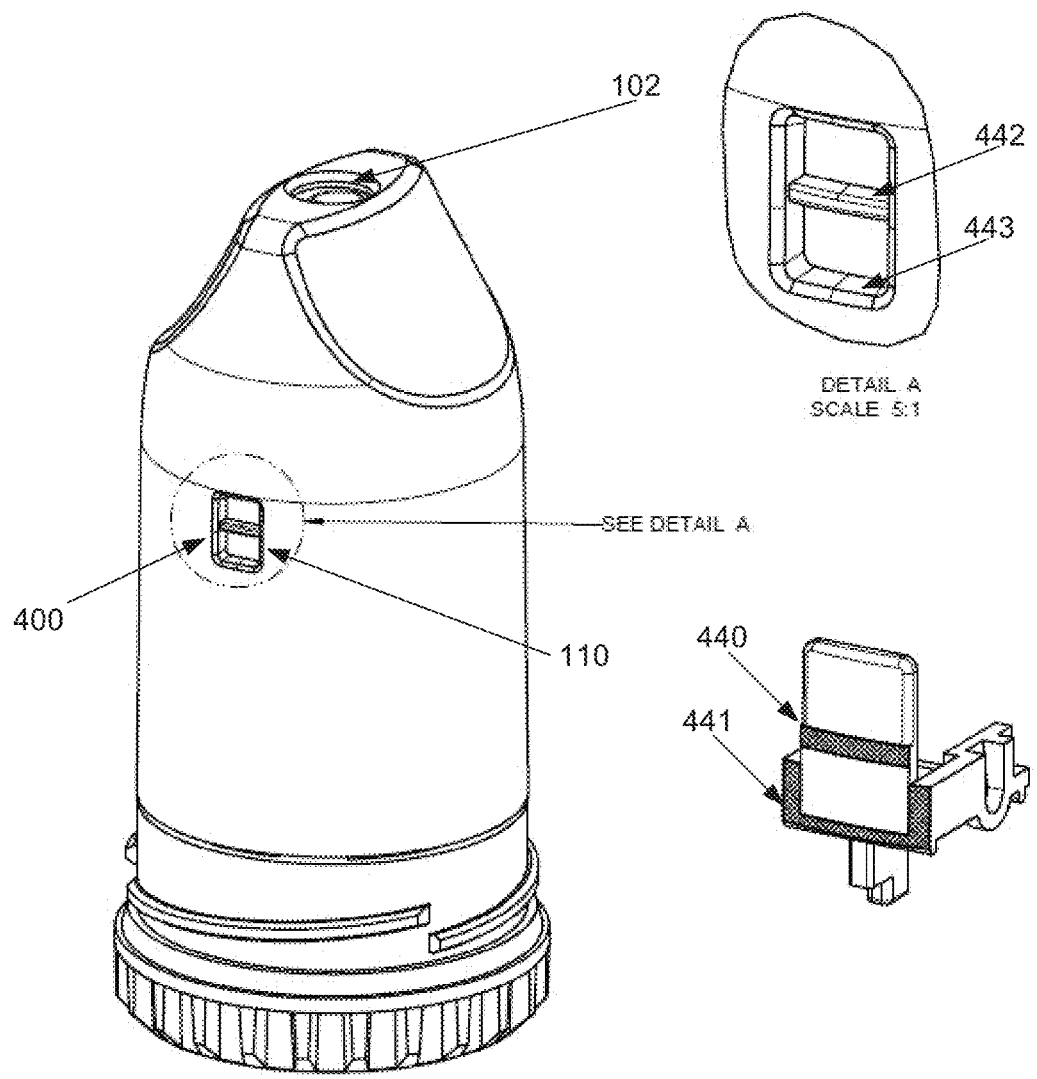
FIG. 21 is a perspective view of the dry powder medicament inhaler showing a positioning of an incorrect dose prevention mechanism at an air inlet.

The pivotable counterweight 420 is dimensioned such that the centre of mass of the pivotable counterweight 420 is distal to the pivoting axis. As can be seen in FIGS. 21 to 23 one way to achieve this is to form a wedge shaped counterweight 420 where the thinner component of the wedge forms the proximal side connecting to the pivoting axis. The distal component is the thicker part of the wedge. The pivotable counterweight 420 can also be provided with a rounded edge at the distal end such that the number of corners is reduced.

Figure 23A:
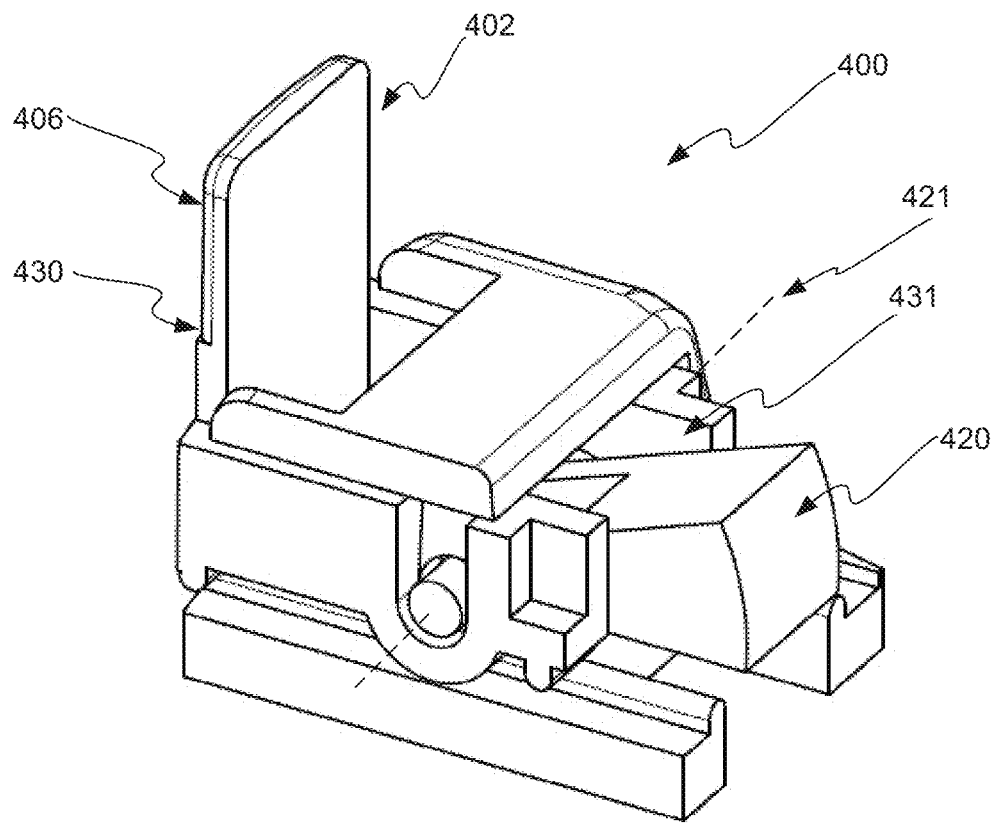
FIG. 23a is a perspective view of an incorrect dose prevention mechanism having a pivotable counterweight being in an outward position.
Figure 23B:
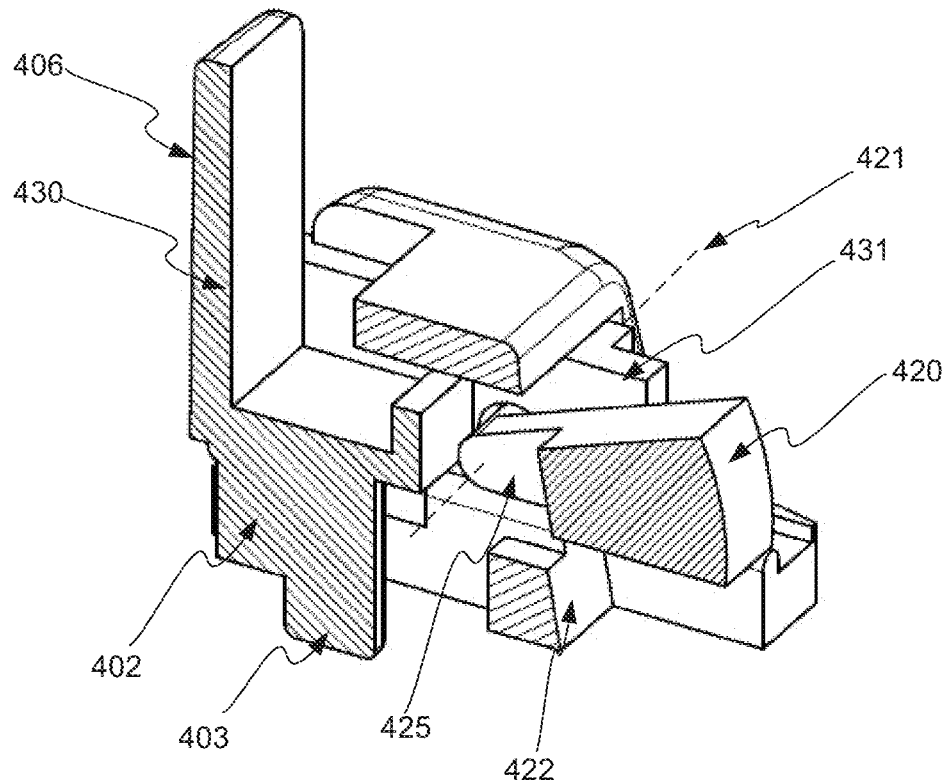
FIG. 23b is a cross sectional perspective view of an incorrect dose prevention mechanism having a pivotable counterweight being in an outward position.
Figure 24A:
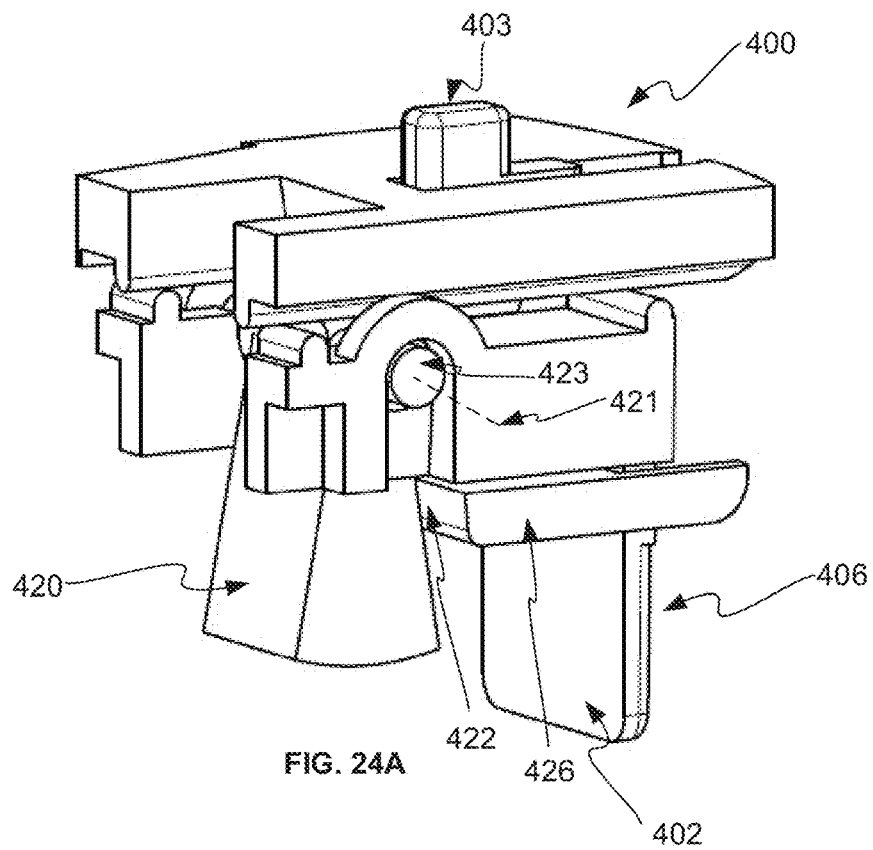
FIG. 24a is a perspective view of an incorrect dose prevention mechanism having a pivotable counterweight in an inverted position.
Figure 24B:
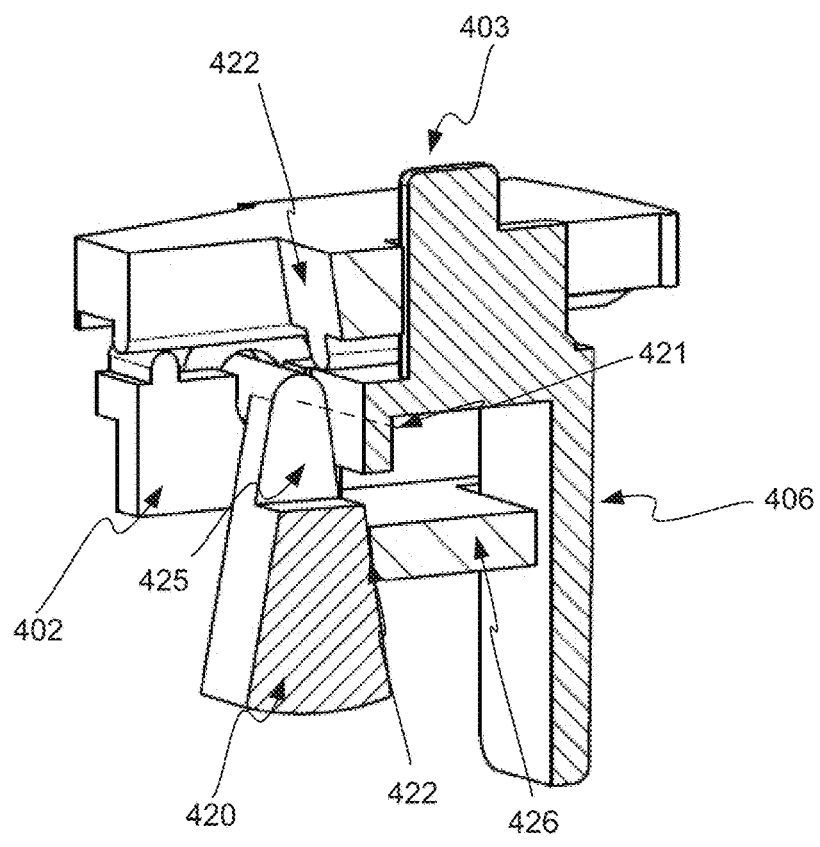
FIG. 24b is a cross sectional perspective view of an incorrect dose prevention mechanism having a pivotable counterweight in an inverted position.

The pivotable counterweight 420 can be connected to the sliding component 402 via at least one pin at the pivoting axis 421. As is shown in FIGS. 22-24 the pivotable counterweight 420 can be connected to the sliding component 402 via two pins 423 extending aligned with the pivoting axis 421. The pins can be insertable into recesses on the sliding component 402.

The pivotable counterweight 420 can be provided with a recess 425 between the pins 423 such that the counterweight can be more easily inserted in to the recesses on the sliding component 402.

The rotating disc 401 is cooperates with the dose disc 104 and twister 105 such that rotation of the dose disc 104 or twister 105 causes rotation of the rotating disc 401. The sliding component can thereby be moved to an outer preventing position.

The dose disc 104 and the rotating disc 401 are arranged substantially parallel and have aligned central axes. The dose disc 104 and the rotating disc 401 can be fixed upon a central shaft. The shaft may be sleeve formed and be arranged on the outside of an inhalation chimney 112. Fixing the rotating disc 401 and the dose disc 104 to a central shaft means that the dose disc 104 and the rotating disc 401 are locked in their rotation. The dose disc 104 and the rotating disc 401 may also be associated by other means such that rotation in one disc causes a rotation in the other.

Figure 19A:
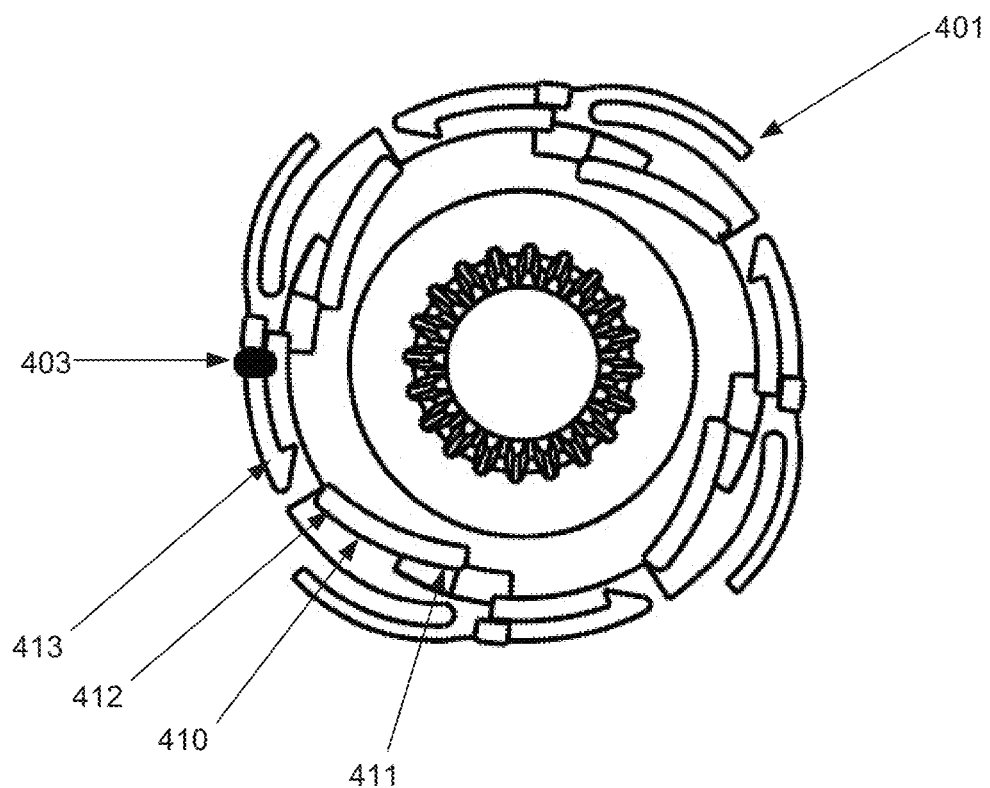
FIG. 19a is a top-down exploded view of the locking disc of an incorrect dose prevention mechanism, being a locking mechanism not having a counterweight.
Figure 19B:
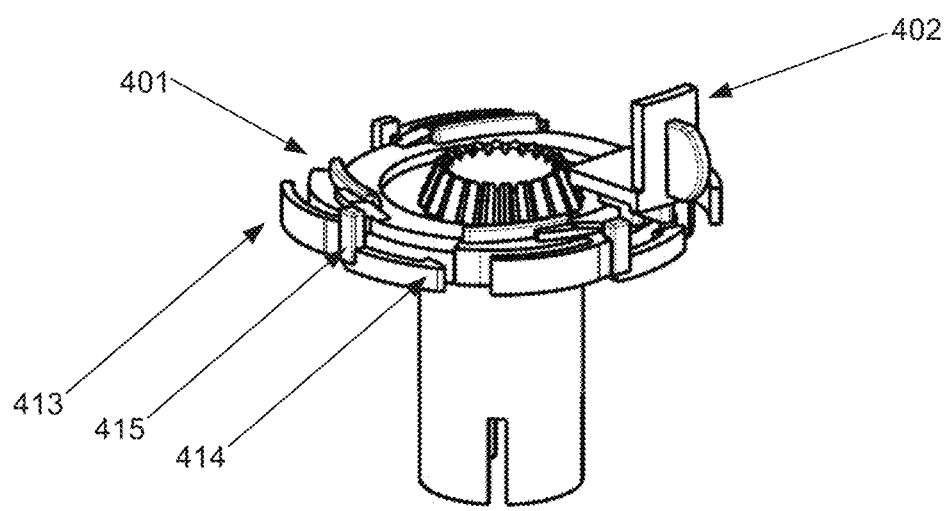
FIG. 19b is a perspective exploded view of the locking disc and latch of the incorrect dose prevention mechanism not having a counterweight.

The rotating disc 401 is shown in FIG. 19. The rotating disc comprises guiding members 410 extending at an angle from the circumference of the rotating disc 401. The guiding members extend in a plane parallel and aligned with the plane formed by the rotating disc 401. The guiding members 410 are arranged such that they are closer to the centre of the rotating disc 401 at a first end 411 than at a second end 412. In FIG. 19B the counterweight according to the invention is not shown.

Figure 20A:
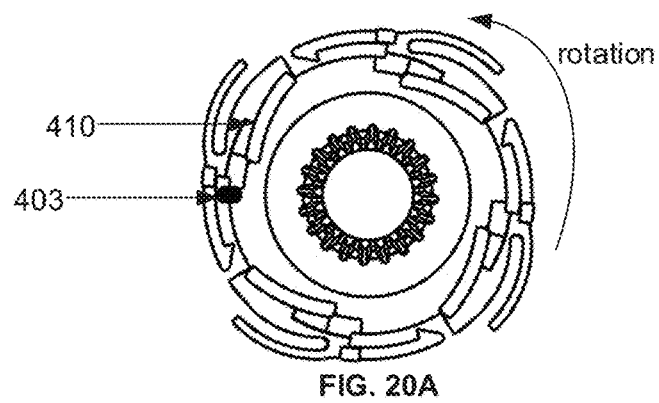
FIGS. 20a-20e are cross sectional exploded views of the incorrect dose prevention mechanism focusing on the indicator and guiding disc during different points of rotation of the guiding disc.
Figure 20B:
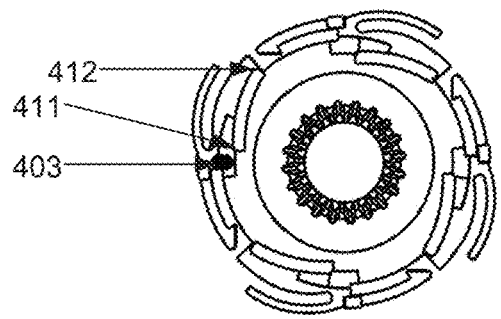
Figure 20C:
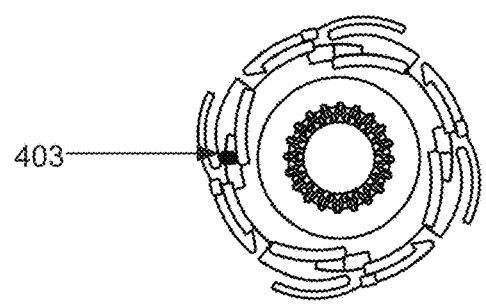
Figure 20D:
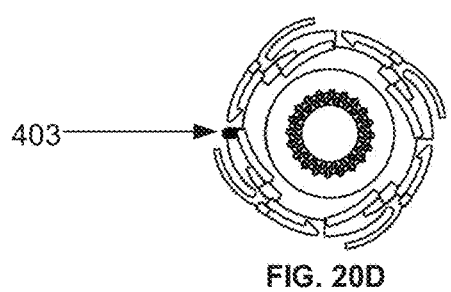
Figure 20E:
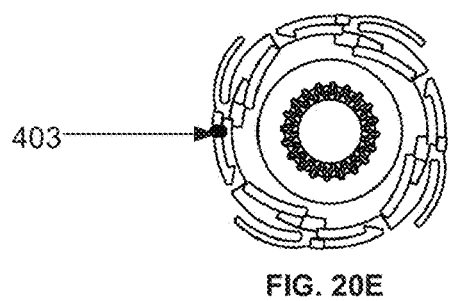

The sliding component 402 is shown in a top down view in FIG. 20a, wherein a projection 403 from the sliding component 402 does not interfere with members of the rotating disc 401. As the dose disc 104 is rotated the rotating disc 401 is also rotated. The first end 411 of the guiding members, being closer to the centre of the rotating disc 401, contacts the projection 403 as shown in FIG. 20b. As the dose disc 104 is further rotated the rotating disc 401 rotates further and the projection 403 slides along the length of the guiding member 410 towards the second end 412 as shown in FIG. 20c. As the second end 412 of the guiding member 410 is further from the centre of the rotating disc, during rotation of the dose disc 104 and the rotating disc 401 the projection 403 and thus the sliding component 402 are moved outwardly from the centre of the rotating disc 401 as shown in FIG. 20d. The sliding component 402 is now in an outer position.

On moving the sliding component 402 outwards then the pivotable counterweight 420 is made to pivot upwards against the downward acting force of gravity. As can be seen in FIGS. 23A and 23B, When the sliding component 402 is an outer, active, preventing position the counterweight rests in a substantially horizontal position.

When resting in a horizontal position the counterweight 420 does not apply a force to the sliding component in an inwards direction. In this way the pivotable counterweight can apply a force only at the start, or during the movement of the incorrect dose prevention mechanism 400. The pivotable counterweight does not provide an inwards force when the incorrect dose preventing mechanism 400 is in a preventing position.

During rotation of the dose disc 104 the dose disc moves from a dose collecting position to a dose administering position. The dose administering position of the dose disc 104 corresponds to the outer, active, preventing position of the incorrect dose prevention mechanism.

One way to move the incorrect dose prevention mechanism 400 from an outer, active, preventing position to an inner, inactive, non-preventing position can be via inhalation at the outlet 102 of the dry powder medicament inhaler 100. This can be called inhalation resetting.

For inhalation resetting the sliding component 402 can be arranged such that inhalation on the dry powder medicament inhaler can cause the sliding component 402 to be moved from an outer, active, preventing position to an inner, inactive, non-preventing position. The sliding component can be positioned at an air inlet 110 on the upper proximal reservoir housing 103.

This is ideal as incorrect dose prevention mechanism can thus be reset after a single dose of medicament has been inhaled.

FIG. 21 shows a view of the dry powder medicament inhaler and one positioning of the incorrect dose prevention mechanism such that inhalation can reset the sliding component 402. On inhalation at the air outlet 102 a general low pressure region is formed inside the dry powder medicament inhaler 100. The low pressure region forms a pressure differential between the region inside the dry powder medicament inhaler 100 and the region external to the dry powder medicament inhaler 100; the pressure inside the dry powder medicament inhaler 100 being lower than the external pressure. The pressure differential can create a force on the sliding component 402 at the air inlet 110 having a direction inwards. This inwardly directed force can cause the sliding component 402 to be moved from an outer, active, preventing state to an inner, inactive, non-preventing state. With such a system the incorrect dose prevention mechanism is reset after a single dose of medicament is inhaled.

FIG. 21 also shows an incorrect dose prevention mechanism having a highly visible coloured band 440. The band can be coloured in a highly visible signalling colour. The coloured band 440 is positioned on the planar face 406 of the sliding component 402. As shown in FIG. 21 the perimeter of the outer region of the sliding component 441 can be provided with a highly visible coloured region. If a coloured region is provided on the face of the sliding component and/or on the surrounding region then the coloured region can be obscured by a beam 442 at the air inlet 110 and by the edge 441 of the air-inlet 110 in a first position, for example, the sliding component being in an outer position. In a second position, there can be a separation between the sliding component and the beam 442 and the edge 441 such that the coloured region is visible. In this way the incorrect dose prevention mechanism is a dosage indicator.

As can be seen in FIG. 24 the pivotable counterweight 420 inhibits the outward movement of the incorrect dose prevention mechanism even if the dry powder medicament inhaler is inverted. In FIG. 24 incorrect dose prevention mechanism has been provided with an upper housing element 426 which forms a stop 422 for the pivotable counterweight 420 when the dry powder medicament inhaler 100 is inverted.

FIGS. 18 and 19 show a dry powder medicament inhaler wherein the incorrect dose prevention mechanism 400 is a locking mechanism 400. The locking mechanism 400 functions such that on moving the dosage mechanism 104, 108 from a dose collecting position to a dose administering position the mechanism 400 is moved from an unlocked position to a locked and position preventing the metering of any further doses prior to resetting of the locking mechanism.

The locking mechanism 400 can restrict the inadvertent metering of multiple doses in to dose metering reservoirs 109,110 as the locking mechanism must be unlocked prior to metering a new dose into the dose metering reservoirs 109,110. The locking mechanism can restrict the intentional misuse of the inhaler by requiring the inhalation of a previously metered dose prior to metering any new dose.

It also enables the user to more quickly ascertain if a dose has been metered by turning the twister 105. If the twister 105 is twistable then a dose had not been metered. If the twister is not twistable, then a dose has already been metered. In this way the incorrect dose prevention mechanism can also prevent the user from inhaling without a dose being present in the dose metering reservoirs 109, 110, thus not receiving any medicament.

As shown in FIG. 18 the locking mechanism 400 comprises a guiding disc, which, when the incorrect dose prevention mechanism is a locking mechanism, can be called a locking disc 401 and a sliding component being a latch 402. The latch 402 is provided with two end positions. An outer locked position A and an inner unlocked position B.

The latch 402 is associated with the locking disc 401 such that a projection 403 from the indicator and latch 402 can, in an outer, active, preventing, locked position A, extend through a plane of the locking disc 401 and be aligned such that that the projection 403 abuts a member or members of the locking disc 401.

In an inner, inactive, non preventing, unlocked position B, the projection 403 from the latch 402 can still extend through the plane of the locking disc 401 but does not abut the member or members of the locking disc 401 such that the locking disc 401 can be rotated.

One way of achieving this is that the projection 403 of the latch 402 in a locked position A is aligned with circumferential members of the locking disc 401 whereas in an unlocked position B the projection 403 of the indicator and latch 402 is out of alignment with the circumferential members of the locking disc such that the locking disc 401 can be rotated. For example, the circumferential members could be the vertical stops 415 disclosed in FIG. 19B.

When the combined indicator and latch 402 is in position A the locking disc 401 cannot rotate and thus the dose disc 104 cannot rotate. When the latch is in position B the locking disc 401 and the dose disc 104 can both rotate.

When the incorrect dose prevention mechanism is a locking mechanism the locking disc 401 further comprises peripheral locking members 413. The peripheral locking members 413 extend from the circumference of the locking disc 401. The peripheral locking members 413 have a base 414 extending parallel to the plane of the locking disc 401 and a vertical stops 415 extending perpendicular to the plane of the locking disc 401. The vertical stop extends 415 substantially vertically. The peripheral locking members 413 are positioned at a distance further from the centre of the locking disc 401 than the guiding members 410. The peripheral locking members are dimensioned such that the projection 403 of the combined indicator and latch 402 can act as a limit to stop any rotation 403 of the locking disc 401 and as they can be fixed to the same shaft, the dose disc 104.

As stated above the incorrect dose prevention mechanism 400 can also be an indicating mechanism whereby the presence or lack thereof of a metered dose is indicated to the user. For example, the indicator mechanism may be a visual indicator such that the user receives visual indication if a dose has previously been metered.

The incorrect dose prevention mechanism can also be a combined indicating and locking mechanism that provides a visual indication of a metered dose and restricts the movement of the dosage mechanism 104, 108.

As described above in respect of FIGS. 1 to 16, the different parts of the dry powder medicament inhaler 100 described in FIGS. 17 to 24 may be manufactured in a suitable material, such as injection moldable plastics, such as thermoplastics.

Although, the present invention has been described above with reference to specific embodiments, it is not intended to be limited to the specific form set forth herein. Rather, the invention is limited only by the accompanying claims.

In the claims, the term "comprises/comprising" does not exclude the presence of other elements or steps. Furthermore, although individually listed, a plurality of means, elements or method steps may be implemented by e.g. a single unit or processor. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second" etc do not preclude a plurality. Reference signs in the claims are provided merely as a clarifying example and shall not be construed as limiting the scope of the claims in any way.

The invention claimed is:

1. A dry powder medicament inhaler for metering an inhalation of dry powdered medicament, comprising:
    at least one inlet and at least one outlet, wherein a communication between said at least one inlet and said at least one outlet at least includes a mixing and deaggregation chamber and at least two dosage communications between the at least one inlet and the chamber;
    a dosage mechanism for arranging at least one dose of a medicament between the inlet and the chamber, such that said at least one dose may be delivered upon inhalation at said outlet through said communications;
    a locking mechanism wherein on moving the dosage mechanism from a dose collecting position to a dose administering position the locking mechanism is moved from an unlocked to a locked position preventing the metering of any further doses prior to resetting of the locking mechanism;
    wherein the locking mechanism includes a locking disc and a latch, and wherein the latch is associated with the locking disc such that a projection from the latch in a locked position extends through a plane of the locking disc, and the projection abuts at least one member of the locking disc.

2. The dry powder inhaler according to claim 1, wherein the locking mechanism is arranged in association with the dosage mechanism such that when locked the locking mechanism restricts the dosage mechanism from rotating.

3. The dry powder medicament inhaler according to claim 1, wherein the latch includes a tab arranged such that a force on the tab moves the latch from a locked position to an unlocked position.

4. The dry powder inhaler according to claim 1, wherein the locking disc and the dosage mechanism are parallel and have aligned rotational axes.

5. The dry powder medicament inhaler according to claim 1, wherein the locking disc includes guiding members extending at an angle from the circumference of the locking disc, wherein the guiding members extend in a plane parallel and aligned with the plane formed by the locking disc, and wherein the guiding members are arranged such that they are closer to the centre of the locking disc at a first end than at a second end.

6. The dry powder medicament inhaler according to claim 1, wherein the latch is arranged such that inhalation on the dry powder inhaler causes the latch to be moved from a locked position to an unlocked position.

7. The dry powder medicament inhaler according to claim 6, wherein the dry powder medicament inhaler further includes an upper proximal reservoir housing, and wherein the latch is positioned at an air inlet on the upper proximal reservoir housing.

8. The dry powder medicament inhaler according to claim 6, wherein inhalation at the air outlet forms a low pressure region inside the dry powder inhaler compared to the outside of the dry powder inhaler, and wherein a pressure differential creates a force on the latch at the air inlet causing the latch to be moved from a locked position to an unlocked position.

9. A dry powder medicament inhaler for metering an inhalation of dry powdered medicament, comprising:
    at least one inlet and at least one outlet, wherein a communication between said at least one inlet and said at least one outlet at least includes a mixing and deaggregation chamber and at least one dosage communication between the at least one inlet and the chamber;
    a dosage mechanism for arranging at least one dose of a medicament between the inlet and the chamber, such that said at least one dose may be delivered upon inhalation at said outlet through said communication;
    a dosage indicator wherein on moving the dosage mechanism from a dose collecting position to a dose administering position the dosage indicator indicates that a dose is ready to be inhaled;
    wherein the dosage indicator further includes a visual indicator arranged to have two states, an indicating state, indicating a dose is ready to be inhaled, and a non-indicating state, indicating there is no dose ready to be inhaled;
    wherein the visual indicator is arranged in association with a rotating disc wherein the rotating disc is associated with a dose disc and a twister such that rotation of the dose disc or the twister causes rotation of the rotating disc and thereby the visual indicator is moved from a non-indicating position to an indicating position; and
    wherein inhalation at the air outlet forms a low pressure region inside the dry powder inhaler compared to the outside of the dry powder inhaler, and wherein the pressure differential can create a force on the visual indicator at the air inlet causing the visual indicator to be moved from the indicating position to the non-indicating position.

10. The dry powder medicament inhaler according to claim 9, wherein the visual indicator is arranged such that inhalation on the dry powder inhaler causes the visual indicator to be moved from the indicating position to the non-indicating position.

11. The dry powder medicament inhaler according to claim 9, wherein the dry powder medicament inhaler further includes an upper proximal reservoir housing and wherein the visual indicator is positioned at an air inlet on the upper proximal reservoir housing.

12. The dry powder medicament inhaler according to claim 11, wherein the visual indicator includes a tab, wherein the tab extends through an opening in the upper proximal reservoir housing when the visual indicator is in an indicating position.

13. The dry powder medicament inhaler according to claim 9, wherein the dosage indicator further acts as a locking mechanism, wherein on moving the dosage mechanism from a dose collecting position to a dose administering position the combined indicating and locking mechanism is moved from an unlocked and non-indicating position to a locked and indicating position preventing the metering of any further doses prior to resetting of the locking mechanism.

14. The dry powder inhaler according to claim 13, wherein the combined indicating and locking mechanism is arranged in association with the dosage mechanism such that when locked the combined indicating and locking mechanism restricts the dosage mechanism from rotating.

15. The dry powder medicament inhaler according to claim 13, wherein the visual indicator is a latch, and the combined indicating and locking mechanism includes a locking disc, wherein the latch is associated with the locking disc such that a projection from the latch in a locked position, extends through a plane of the locking disc and is aligned such that the projection abuts at least one member of the locking disc.

16. A dry powder medicament inhaler for metering an inhalation of dry powdered medicament, comprising:
- at least one inlet and at least one outlet, wherein a communication between said at least one inlet and said at least one outlet at least includes a mixing and deaggregation chamber and at least one dosage communication between the at least one inlet and the chamber;
- a dosage mechanism for arranging at least one dose of a medicament between the inlet and the chamber, such that said at least one dose may be delivered upon inhalation at said outlet through said communication;
- an incorrect dose prevention mechanism arranged in cooperation with the dosage mechanism such that on moving the dosage mechanism from a dose collecting position to a dose administering position the incorrect dose prevention mechanism is activated; and
- a pivotable counterweight associated with the incorrect dose prevention mechanism such that the pivotable counterweight inhibits the activation of the incorrect dose prevention mechanism;
- wherein the incorrect dose prevention mechanism includes a sliding component, the sliding component being arranged in association with a rotating disc, and wherein the rotating disc is associated with a dose disc and twister such that rotation of the dose disc or twister causes rotation of the rotating disc and thereby the sliding component is activated and moved outwardly.

17. The dry powder inhaler according to claim 16, wherein the counterweight does not provide an inwards force when the incorrect dose prevention mechanism is in an outer position.

18. The dry powder inhaler according to claim 16, wherein the incorrect dose prevention mechanism is a dosage indicator.

19. The dry powder inhaler according to claim 16, wherein the incorrect dose prevention mechanism is a locking mechanism.

20. The dry powder inhaler according to claim 16, wherein the incorrect dose prevention mechanism is a locking mechanism and a dosage indicator.

21. The dry powder medicament inhaler according to claim 16, wherein the pivotable counterweight is associated with a stop such that the mass of the counterweight acts on the stop to inhibit outward movement of the incorrect dose prevention mechanism.

22. The dry powder inhaler according to claim 21, wherein the stop is declined with respect to the longitudinal axis of the dry powder medicament inhaler.

23. The dry powder medicament inhaler according to claim 16, wherein the pivotable counterweight pivots around an axis positioned at the inner part of the sliding component.

24. The dry powder medicament inhaler according to claim 23, wherein the pivotable counterweight extends from the axis toward the longitudinal axis of the dry powder medicament inhaler from the sliding component.

25. The dry powder medicament inhaler according to claim 24, wherein the pivotable counterweight is dimensioned such that the centre of mass of the pivotable counterweight is distal to the pivoting axis.

* * * * *